United States Patent [19]

Yoshioka et al.

[11] 3,997,528
[45] Dec. 14, 1976

[54] CEPHALOSPORIN COMPOUNDS

[75] Inventors: Mitsuru Yoshioka, Toyonaka; Masayuki Murakami, Itami; Yuji Sendo, Nishinomiya; Sadao Miyazaki, Toyonaka; Koji Ishikura, Amagasaki; all of Japan

[73] Assignee: Shionogi & Co., Ltd., Osaka, Japan

[22] Filed: Oct. 22, 1974

[21] Appl. No.: 517,483

[30] Foreign Application Priority Data

Oct. 25, 1973 Japan ............................. 48-12032

[52] U.S. Cl. ........................ 260/240 G; 424/246; 260/243 C
[51] Int. Cl.[2] ...................................... C07D 501/20
[58] Field of Search ................. 260/243 C.

[56] References Cited

UNITED STATES PATENTS 3,516,997   6/1970   Takano et al. .................. 260/243 C
3,872,115   3/1975   Sugimoto et al. .............. 260/243 C

*Primary Examiner*—Nicholas S. Rizzo
*Attorney, Agent, or Firm*—Wenderoth, Lind & Ponack

[57] ABSTRACT

Antibacterial cephalosporin compounds of the following formula:

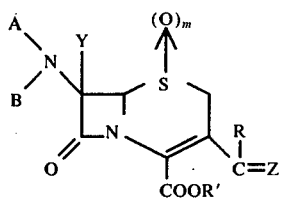

wherein A and B each is a hydrogen, organic or inorganic acyl, or A and B combined together are a diacyl group derived from a polybasic acid; Y is a hydrogen or methoxy; R is a hydrogen or lower alkyl; R' is a hydrogen, alkali metal, organic base group or easily removable protecting group; $m$ is 0 or 1; Z is an optionally substituted guanylhydrazono group, preparable from the corresponding oxo compound or its reactive derivative by reacting with a guanylhyrazine of the formula $H_2Z$ or its reactive derivative, or by some other reactions.

12 Claims, No Drawings

CEPHALOSPORIN COMPOUNDS

This invention relates to a novel antibacterial cephalosporin compound (I) represented by the following formula, a process for preparing the compound, and a pharmaceutical composition containing the compound as an active ingredient.

The cephalosporin compounds of this invention are represented by the following formula:

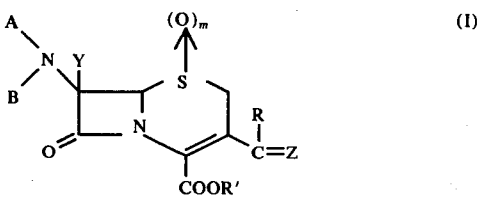

wherein A and B each is a hydrogen, organic or inorganic acyl, or A and B combined together are a diacyl group derived from a polybasic acid; Y is a hydrogen or methoxy; R is a hydrogen or lower alkyl; R' is a hydrogen, alkali metal, organic base group, or an easily removable protecting group; m is an integer 1 or zero; and Z is a optionally substituted guanylhydrazono group of the formula

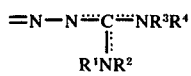

(in which $R^1$, $R^2$, $R^3$, and $R^4$ each is a hydrogen, alkanoyl containing 1 to 8 carbon atoms, hydroxy, amino, nitro, carbamoyl, thiocarbamoyl, lower alkanoylamino containing 1 to 8 carbon atoms, alkyl, alkoxy, alkenyl, alkynyl, aryl, aralkyl, or aralkenyl containing 1 to 8 carbon atoms optionally interrupted by a hetero atom selected from nitrogen, oxygen, and/or sulfur, and optionally substituted by an inert group such as alkyl, carboxy, carbalkoxy, alkanoylamino, alkanoyl, alkanoyloxy, or alkoxy containing 1 to 8 carbon atoms, amino, nitro, hydroxy, mercapto, oxo, thioxo, or halogen: two or more of $R^{1-4}$ can be combined together where possible).

The compound (I) is a strongly active broad spectrum antibacterial against Gram positive and negative bacteria, especially against Streptococci, Diplococci, Enterococci, Escherlichia, klebsiella, Proteus, and other bacteria.

In the formula (I), A and B each is a hydrogen, organic or inorganic acyl, or A and B combined together are a diacyl group derived from a polybasic acid. The acyl group represented by A or B includes so-called side chains of known penicillins and cephalosporins.

Some of the preferable acyl groups for the groups A and B are included in the following:

1. $ArCH_2CO-$: where Ar is a phenyl, dihydrophenyl, or monocyclic heterocyclic aromatic group containing 1 to 4 hetero atoms selected from nitrogen, oxygen, and/or sulfur atoms, and optionally be substituted by an inert group e.g. an alkyl containing 1 to 3 carbon atoms, hydroxy, halogen, aminomethyl, or alkoxy containing 1 to 3 carbon atoms;

2. $Ar-L-CH_2CO-$: where Ar is as defined above, and L is an oxygen, sulfur, or imino;

3. $Ar-CH(W)-CO-$: where Ar is as defined above, and W is an azido, hydroxy, mercapto, carboxy, sulfo, or halogen, which can be protected by a manner known to those skilled in the art (e.g. esters for hydroxy, mercapto, carboxy, and sulfo);

4. $Q-O-CO-$: where Q is an easily removable optionally substituted hydrocarbon group. The group is known to those skilled in the art as amino-protecting groups (e.g. the group where Q is 2,2,2-trichloroethyl, isobornyl, tertiary butyl, 1-methylcyclohexyl, 2-alkoxy-tertiary butyl, benzyl, p-nitrobenzyl, p-methoxybenzyl, or like groups);

5. alkanoyl containing 1 to 8 carbon atoms (e.g. formyl, acetyl, butyryl, octyl);

6. ω-aminoadipoyl group optionally protected at its carboxy or amino group (e.g. as esters, amides, etc.);

7. diacyl group derived from polybasic carboxylic acid containing 1 to 10 carbon atoms;

8. aromatic sulfenyl group optionally substituted by an inert group (e.g. o-nitrophenylsulfenyl, phenylsulfenyl); and 9. cyanoacetyl group.

Some of the more preferable groups

for the compound (I) include the group $Ar-CH_2CONH-$ or $Ar-CH(W)-CONH-$ where Ar is a furyl, thienyl, pyrryl, oxazolyl, oxadiazolyl, oxatriazolyl, isoxyazolyl, thiazolyl, thiadiazolyl, thiatriazolyl, isothiazolyl, pyrazolyl, imidazolyl, triazolyl, tetrazolyl, phenyl, pyridyl, pyrimidyl, pyrazinyl, pyridazinyl, triazinyl, or dihydrophenyl, optionally substituted by a hydroxy, halogen, aminomethyl or methyl; and W is a hydroxy.

When both of A and B are hydrogens, the compound (I) is useful as intermediates for the synthesis of other anti-bacterial compounds (I).

Y is a hydrogen or methoxy. Among them, hydrogen is more preferable than methoxy. The methoxy has better influence on the activity of the compound (I) against indole positive Proteus.

R is a hydrogen or a lower alkyl. For this group, hydrogen is better than the lower alkyl, among which methyl is the most preferable.

R' is a hydrogen, alkali metal (e.g. lithium, sodium, potassium), pharmaceutically acceptable organic base group (e.g. triethylammonium, dimethylammonioethanol, procain), or an easily removable protecting group. The pharmaceutically acceptable salts are salts effective and non-toxic at the used dose level (e.g. alkali metal salts or some organic base salts cited above). When the group R' is an easily removable protecting group, the compound (I) is useful as an intermediate, or in some cases as lower acyloxymethyl esters, phenacyl esters, and like groups, it is useful as a drug for oral or parenteral administration. Typical examples of the easily removable protecting groups are those forming an alkyl ester (e.g. methyl, tertiary butyl esters), halo-lower alkyl ester (e.g. 2-chloroethyl, 2,2,2-trichloroethyl esters), lower acyl-lower alkyl ester (e.g. lower alkanoylmethyl, 2-acetylethyl, phenacyl, p-bromophenacyl, α-benzoylbenzyl esters), lower alkoxy-lower alkyl ester (e.g. methoxymethyl ester), lower acyloxy-lower alkyl ester (e.g. acetoxymethyl, pivaloyloxymethyl, N,N-dimethylglycyloxymethyl, benzoyloxymethyl esters), lower 1,1-dicarbo-lower alkoxyalkyl ester (e.g. dicarbomethoxymethyl, dicarbethoxymethyl esters), lower aryl ester (e.g. phenyl, pyridyl esters optionally substituted by an inert group e.g. nitro, methoxy, or lower alkyl), aralkyl ester (e.g. benzyl, benzhydryl, naphthylmethyl, and pyridylmethyl esters optionally substituted by an inert group), ester with a hydroxylamine or oxime derivative, or their equivalents, and other groups known to those skilled in the art.

The symbol $m$ is an integer 1 or zero. The sulfoxide where $m$ is 1 is useful as an intermediate for the synthesis of compound (I) or for the stabilization of the double bond at position 3.

The group Z is an optionally substituted guanylhydrazono group as defined above. When one or more of $R^1$, $R^2$, $R^3$, and $R^4$ is a hydrogen, the position of the double bond from the carbon to adjacent nitrogens are mobile from one to other nitrogens, and the structure of the products imply the presence of position isomers. Structure of the main or sole isomer depends on the nature of product and on the method of preparation.

The group Z can be in a form of salts with intra- or intermolecular acid groups.

Preferable groups Z are those where $R^3$ and/or $R^4$ is a hydrogen, and the group $-NR^1R^2$ is that included in the following groups:

1. hydrazin-1-yl, 1-alkylhydrazin-1-yl containing 1 to 3 carbon atoms, 2-alkylhydrazin-1-yl containing 1 to 3 carbon atoms, nitroamino, hydroxyamino, or alkoxyamino containing 1 to 6 carbon atoms;

2. amino, alkylamino containing 1 to 6 carbon atoms, or alkenylamino containing 2 to 6 carbon atoms;

3. arylamino containing 6 to 9 carbon atoms, or aralkylamino containing 7 to 10 carbon atoms;

4. dialkylamino containing 2 to 12 carbon atoms, dialkenylamino containing 2 to 12 carbon atoms, diaralkylamino containing 14 to 18 carbon atoms, N-alkyl-N-alkoxyamino, or N-hydroxy-N-alkylamino containing 1 to 4 carbon atoms, or N-alkyl-N-arylamino containing 7 to 12 carbon atoms;

5. a group of the following formula:

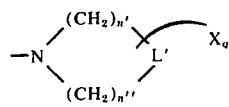

where L' is an oxygen, sulfur, methylene, imino, or acylimino containing 1 to 8 carbon atoms; $n'$ and $n''$ each is an integer or zero, provided $n'+n''$ being 2 to 6; X is an alkyl containing 1 to 3 carbon atoms, oxo, oxy, or halogen; and $q$ is zero or an integer 1 to 3;

6. a group of the following formula:

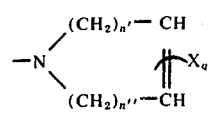

where X, $q$, $n'$ and $n''$ are as defined above; and like groups.

Among these groups for the group $-NR^1R^2$ the more preferable groups are these cited in (5) and (6)

above, and dialkylamino containing 1 to 3 carbon atoms classified in (4) above.

One of the most preferable group $-NR^1R^2$ is morpholin-4-yl, piperidin-1-yl or 1-azacycloheptan-1-yl, optionally substituted by a methyl group.

Preferable antibacterial compounds (I') are represented by the following formula:

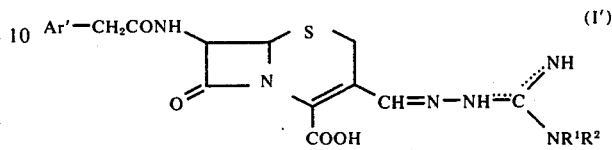

wherein Ar' is a furyl, thienyl, pyrryl, oxazolyl, isoxazolyl, oxadiazolyl, oxatriazolyl, thiazolyl, thiadiazolyl, thiatriazolyl, isothiazolyl, pyrazolyl, imidazolyl, triazolyl, tetrazolyl, phenyl, pyridyl, pyrimidyl, pyrazinyl, pyridazinyl, triazinyl, or dihydrophenyl, optionally substituted by a hydroxy, halogen, or methyl; and $-NR^1R^2$ is a ring system group selected from the following groups: (1) pyrrolidin-1-yl, (2) piperidin-1-yl, (3) 1-azacycloheptan-1-yl, (4) pyrrolin-1-yl, (5) tetrahydropyridin-1-yl, (6) morpholin-4-yl (tetrahydro-1,4-oxazin-4-yl), (7) tetrahydro-1,2-oxazin-2-yl, (8) tetrahydro-1,3-oxazin-3-yl, (9) tetrahydroisoxazol-2-yl, (10) tetrahydrooxazol-3-yl, (11) tetrahydroisothiazol-2-yl, (12) tetrahydrothiazol-3-yl, (13) tetrahydro-1,3-thiazin-3-yl, and (14) thiamorpholin-4-yl (tetrahydro-1,4-thiazin-4-yl) ring system group, and their pharmaceutically acceptable salts. The ring system $-NR^1R^2$ can possess an inert substituent, e.g. alkyl containing 1 to 6 carbon atoms, oxo, hydroxy, halogen, carbalkoxy, or carbamoyl. The compounds (I') are more effective antibacterials against Enterococci than commercial cephalosporins.

More preferable compounds have a furyl, thienyl, isoxazolyl, tetrazolyl, or phenyl for the group Ar'; and tetrahydro-1,4-oxazin-4-yl optionally substituted by methyl group for the group $-NR^1R^2$ which are strongly active against a Gram negative bacteria especially against a cephalosporing resistant strain of Escherlichia coli, or have a pyrrolidin-1-yl, piperidin-1-yl, or 1-azacycloheptan-1-yl for the group $-NR^1R^2$ which are strongly active against indole positive Proteus.

Preferable compounds (I') include following sets of compounds:

1. A compound (I') where $-NR^1R^2$ is a pyrrolidin-1-yl, piperidin-1-yl, or 1-azacycloheptan-1-yl ring system group, for example, 7-(2-thienylacetamido)-3-(4,4-tetramethyleneguanylhydrazono)methyl-3-cephem-4-carboxylic acid,
7-(2-thienylacetamido)-3-(4,4-pentamethyleneguanylhydrazono)methyl-3-cephem-4-carboxylic acid,
7-(2-thienylacetamido)-3-(4,4-hexamethyleneguanylhydrazono)methyl-3-cephem-4-carboxylic acid,
7-phenylacetamido-3-(4,4-pentamethyleneguanylhydrazono)methyl-3-cephem-4-carboxylic acid,
and their pharmaceutically acceptable salts.

2. A compound (I') where $-NR^1R^2$ is a pyrrolin-1-yl, or tetrahydropyridin-1-yl ring system group, for example, 7-(2-thienylacetamido)-3-[4,4-(but-2-en-1,4-diyl)-guanylhydrazono]methyl-3-cephem-4-carboxylic acid, 7-(2-thienylacetamido)-3-[4,4-(pent-2-en-1,5-diyl)-guanylhydrazono]methyl-3-cephem-4-carboxylic acid, and their pharmaceutically acceptable salts.

3. A compound (I') where —NR¹R² is a tetrahydro-1,4-oxazin-4-yl (morpholin-4-yl) ring system group, for example, 7-(2-thienylacetamido)-3-[4,4-(3-oxapentamethylene)guanylhydrazono]methyl-3-cephem-4-carboxylic acid, 7-(2-thienylacetamido)-3-[4,4-(1-methyl-3-oxapentamethylene)guanylhydrazono]methyl-3-cephem-4-carboxylic acid, 7-(2-thienylacetamido)-3-[4,4-(2-methyl-3-oxapentamethylene)guanylhydrazono]methyl-3-cephem-4-carboxylic acid, 7-(2-thienylacetamido)-3-[4,4-(1,4-dimethyl-3-oxapentamethylene)guanylhydrazono]methyl-3-cephem-4-carboxylic acid, 7-(2-thienylacetamido)-3-[4,4-(2,4-dimethyl-3-oxapentamethylene)guanylhydrazono]methyl-3-cephem-4-carboxylic acid, 7-(2-thienylacetamido)-3-[4,4-(2-ethyl-3-oxapentamethylene)guanylhydrazono]methyl-3-cephem-4-carboxylic acid, 7-phenylacetamido-3-[4,4-(3-oxapentamethylene)-guanylhydrazono]methyl-3-cephem-4-carboxylic acid, 7-(2-furylacetamido)-3-[4,4-(3-oxapentamethylene)-guanylhydrazono]methyl-3-cephem-4-carboxylic acid, 7-(3-thienylacetamido)-3-[4,4-(3-oxapentamethylene)guanylhydrazono]methyl-3-cephem-4-carboxylic acid, 7-(3-isoxazolylacetamido)-3-[4,4-(3-oxapentamethylene)guanylhydrazono]methyl-3-cephem-4-carboxylic acid, 7-(1-tetrazolylacetamido)-3-[4,4-(3-oxapentamethylene)guanylhydrazono]methyl-3-cephem-4-carboxylic acid, and their pharmaceutically acceptable salts, 4. A compound (I') where —NR¹R² is a tetrahydro-1,2-oxazin-2-yl, tetrahydro-1,3-oxacin-3-yl, tetrahydrothiazin-4-yl, tetrahydrothiazol-3-yl, tetrahydroisoxazol-2-yl, tetrahydrooxazol-3-yl, or tetrahydroisothiazol-2-yl ring system group, for example, 7-(2-thienylacetamido)-3-[4,4-(1-oxapentamethylene)guanylhydrazono]methyl-3-cephem-4-carboxylic acid, 7-(2-thienylacetamido)-3-[4,4-(2-oxapentamethylene)guanylhydrazono]methyl-3-cephem-4-carboxylic acid, 7-(2-thienylacetamido)-3-[4,4-(3-thiapentamethylene)guanylhydrazono]methyl-3-cephem-4-carboxylic acid, 7-(2-thienylacetamido)-3-[4,4-(2-thiatetramethylene)guanylhydrazono]methyl-3-cephem-4-carboxylic acid, 7-(2-thienylacetamido)-3-[4,4-(1-oxatetramethylene)guanylhydrazono]methyl-3-cephem-4-carboxylic acid, 7-(2-thienylacetamido)-3-[4,4-(2-oxatetramethylene)-guanylhydrazono]methyl-3-cephem-4-carboxylic acid, and their pharmaceutically acceptable salts.

Among other antibacterial compounds (I) prepared in the Examples, following compounds are more useful:

7-(2-thienylacetamido)-3-(4-nitroguanylhydrazono)-methyl-3-cephem-4-carboxylic acid, 7-(2-thienylacetamido)-3-(4-aminoguanylhydrazono)-methyl-3-cephem-4-carboxylic acid, 7-(2-thienylacetamido)-3-(4-methoxyguanylhydrazono)methyl-3-cephem-4-carboxylic acid, 7-(2-thienylacetamido)-3-(4-methylguanylhydrazono)methyl-3-cephem-4-carboxylic acid, 7-(2-thienylacetamido)-3-(4-ethylguanylhydrazono)-methyl-3-cephem-4-carboxylic acid, 7-(2-thienylacetamido)-3-(4-allylguanylhydrazono)-methyl-3-cephem-4-carboxylic acid, 7-(2-thienylacetamido)-3-guanylhydrazonomethyl-3-cephem-4-carboxylic acid, 7-(2-thienylacetamido)-3-(4,4-dimethylguanylhydrazono)methyl-3-cephem-4-carboxylic acid, 7-(2-thienylacetamido)-3-(4,4-diethylguanylhydrazono)methyl-3-cephem-4-carboxylic acid, 7-(2-thienylacetamido)-3-(4,4-diallylguanylhydrazono)methyl-3-cephem-4-carboxylic acid, 7-(2-thienylacetamido)-3-(3,4-ethyleneguanylhydrazono)methyl-3-cephem-4-carboxylic acid, 7-(2-thienylacetamido)-3-[3,4-(1-oxoethylene)guanylhydrazono]methyl-3-cephem-4-carboxylic acid, 7-(2-thienylacetamido)-3-[3,4-(1-thioxoethylene)-guanylhydrazono]methyl-3-cephem-4-carboxylic acid, and their pharmaceutically acceptable salts.

Other useful antibacterial and intermediate compounds (I) having conventional amino protecting group at 7-amino group include the following compounds:

7-tertiary butoxycarbonylamino-3-[4,4-(3-oxapentamethylene)guanylhydrazono]methyl-3-cephem-4-carboxylic acid.

7-(2,2,2-trichloroethoxycarbonyl)amino-3-[4,4-(3-oxapentamethylene)guanylhydrazono]methyl-3-cephem-4-carboxylic acid, 7-(o-nitrophenylsulfenyl)amino-3-[4,4-(3-oxapentamethylene)guanylhydrazono]methyl-3-cephem-4-carboxylic acid, 7-amino-3-[4,4-(3-oxapentamethylene)guanylhydrazono]methyl-3-cephem-4-carboxylic acid, and like compounds, and their salts and esters.

The compound (I) is preparable by the methods exemplified in the following descriptions:

1. Reaction of an oxo compound (II) of the following formula:

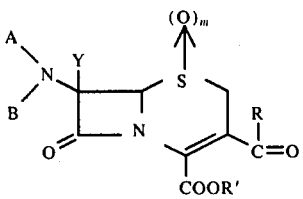

wherein A, B, R, R', Y and m are as defined above, or its reactive derivative with a hydrazine compound (III) H₂Z (wherein Z is as defined above) or its reactive derivative affords a cephalosporin compound (I). The oxo compound (II) can be prepared by e.g. oxidation of the corresponding 3-oxymethylcephem compound. The reactive derivative of the oxo compound (II) ca be an acetal (dialkylacetal, diacylacetal, hemiacetal, intramolecular hemiacetal lactone with the carboxy group at position 4, and the like compounds) or other derivatives capable of producing the hydrazone compounds (I) by the reaction with a hydrazine compound (III) or its reactive derivative. The hydrazine compound (III) is a known substance or a compound derivable from a known compound by conventional methods. The reactive derivative of the hydrazine compound (III) include a salt with an acid, N-acyl derivative, alkylidene derivative or other derivatives capable of producing a hydrazone compound (I) by the reaction with the oxo compound (II) or its reactive derivative. The oxo compound (II) or its reactive derivative is brought to contact with the hydrazine compound (III) or its reactive derivative to give the objective cephalosporin compound (I), preferably in a solvent. The solvent includes a hydrocarbon, halohydrocarbon, ether, ester, alcohol, carboxylic acid, base, amide, nitrile, nitrohydrocarbon, sulfoxide, water, and other conventional solvents or their mixture. Preferable solvents include an ether (tetrahydrofuran, tetrahydropyran, ethyleneglycol dimethyl ether, and other ether solvents), amide (dimethylformamide, dimethylacetamide, and other amide solvents), sulfoxide (dimethylsulfoxide and other sulfoxide solvents), water, and their mixtures. The reaction can be done at an elevated temperature, room temperature, or cooled temperature. Into the reaction medium can be added an acid or base, for regulation of pH, or as a catalyzer. The acid addition salt of the hydrazine compound (III) can be used instead. Reaction is more rapid under neutral or weakly acid condition. The medium can be stirred, or kept under inert gas. The medium can be uniform or heterogeneous. The reaction proceeds through an intermediate, the corresponding 3-(α-hydroxy-α-hydrazinoalkyl)cephem-derivatives.

2. Conventional acylation of a compound (I'') of the following formula:

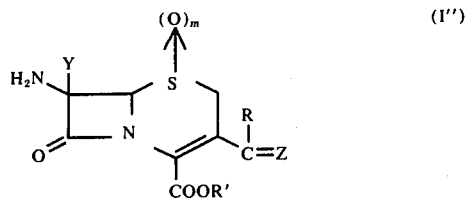

wherein R, R', Y, Z and m are as defined above with an acylating reagent for the introduction of the corresponding acyl group A or B gives the corresponding cephalosporin compound (I). The acylating reagent can be an acid in the presence of condensing reagent, a halide, anhydride, reactive ester, reactive amide, or azide of an acid having the desired acyl group A or B.

3. The acyl group A and/or B of the compound (I) can be removed by a conventional method e.g. hydrolysis, hydrogenolysis, reduction, and other methods conventional in the art to give the compound (I'') above. The methods include treatment with acid for carbonic acyl or sulfenyl, reduction with metal for 2,2,2-trichloroethoxycarbonyl, or hydrogenolysis for carbobenzoxy group. Hydrolysis through iminoether or iminohalide may also be applicable.

4. When the carboxy substituent R' of the compound (I) is a salt, it can be replaced by conventional cation exchange to give another salt or free acid. Such methods include treatment with an acid or base, including ion exchange resins, and a salt of strong base with a weak acid.

5. When R' of the compound (I) is an easily removable protecting group, it can be replaced with a hydrogen by conventional method including treatment with trifluoroacetic acid and anisole for diphenylmethyl group, hydrogenation for benzyl groups, reduction with zinc for 2,2,2-trichloroethyl group, or acid for salts or organometallic esters.

6. When m of the compound (I) is zero, the compound can be oxidized by conventional methods in the art to give a compound where m is 1. The method includes oxidation with peracids, their salts, hydrogen peroxide, ozone and other oxidizing reagents.

7. When m of the compound (I) is 1, the compound can be reduced by a conventional method in the art to give a compound where m is zero. The method includes reduction with reducing inorganic salts (thiosulfites, iodides, stannous salts, ferrous salts), phosphines, and other reducing reagents.

8. Some compounds (I) can be converted to other compounds (I) by introducing or removing protecting groups in the molecule by conventional methods in the art.

The products of the reactions cited above can be isolated and purified by e.g. extraction, concentration, precipitation, absorption, elution, reprecipitation, recrystallization, chromatography, lyophillization, counter-current distribution, and other methods conventional in the art.

The antibacterial products (I) can be used as medicines for humans and warm blooded animals optionally in admixture with a conventional pharmaceutical carrier. They can be used externally, orally, or parenterally, for the prevention or treatment of bacterial infection caused by sensitive Gram positive or negative bacteria, especially weakly cephalosporin-resistant Escherlichia, indole positive and negative Proteus, and Enterococci, at a dose of 0.01 to 0.1 g per kilogram body weight per day, preferably in a unit dosage form. They can be used for the treatment of plant diseases caused by bacteria, or for the prevention of or stopping decay of perishables. They are also useful as intermediates for the production of other anti-bacterials. The pharmaceutical carrier for the compound (I) can be a solid or liquid in which the compound is dispersed, dissolved, or suspended. Solid compositions can take the form of tablets, powders, vials, granules, capsules, pills, or like forms. Liquid composition can take the form of injections, ointments, suspensions, solutions, emulsions, syrups, elixirs, or like forms conventional in the art. The carriers include diluents (e.g. starch, sucrose, lactose, calcium carbonate, kaolin); bulking agents (e.g. lactose, salt, glycine, starch); binders (e.g. starch, acacia, gelatin, glucose, sodium alginate, tragacanth, carboxymethylcellulose); disintegrators (e.g. starch, agar, carbonates); lubricants (e.g. stearic acid, talc, parafin, boric acid, sodium benzoate, cacao oil); ointment bases (e.g. fats, oils); emulsifying agents; solvents (e.g. water, polyethylene glycol, olive oil, sesame oil, cacao oil, methyl or ethyl oleate); solubilizing reagents; buffers; and stabilizing agents. Vials for injection and capsules for oral administration can contain powder, lyophyllizate, or crystals of the compound (I) (0.1 to 10 g), together with additives such as stabilizers or co-acting substances, if required.

The following examples represent presently-preferred embodiment of this invention, but it is to be understood that the examples are given by way of illustration only and not of limitation. The elemental analyses of the compounds as prepared show good agreement with the calculated values. EtOH is for ethanol, and DMSO is for dimethyl sulfoxide.

EXAMPLE I-1.

To a solution of p-nitrobenzyl 3-formyl-7-tertiary butoxycarbonylamino-3-cephem-4-carboxylate (92.7 mg) in tetrahydrofuran (4.6 ml) is added a solution of 4,4-(3-oxapentamethylene)guanylhydrazine hydrobromide (90 mg) in water (1 ml), and the mixture is kept at room temperature for 16.5 hours. The reaction mixture is concentrated, and formed crystals are collected by filtration, washed with water, and dried to give p-nitrobenzyl 3-[4,4-(3-oxapentamethylene)guanylhydrazono]-methyl-7-tertiary butoxycarbonylamino-3-cephem-4-carboxylate (85mg). m.p. 180°–188° C (decomp.). Yield: 72%. IR: $\nu_{max}^{CHCl_3}$ 3435, 3300, 3175, 1797, 1728, 1650, 1609, 1500, 1350 cm$^{-1}$. UV: $\lambda_{max}^{EtOH}$ 266nm ($\epsilon$=13400); 330nm ($\epsilon$=18200). NMR: $\delta^3$-DMSO (60 MHz) 1.41 s9H, 3.2-3.8br10H, 5.22d(5Hz)1H, 5.46br-s1H.

In a procedure similar to that described above, the following compounds are prepared from the corresponding 3-formylcephem-4-carboxylates and guanylhydrazine salts:

1. diphenylmethyl 3-[4,4-(3-oxapentamethylene)-guanylhydrazono]methyl-7-(2-thienylacetamido)-3-cephem-4-carboxylate 1-oxide monohydrate, m.p. 185°–188° C (decomp.). IR: $\nu_{max}^{Nujol}$ 3440, 3305, 1781, 1710, 1665, 1600, 1573, 1500 cm$^{-1}$. UV: $\lambda_{max}^{EtOH}$ 384nm ($\epsilon$=22000). NMR: $\delta^{CDCl_3+CD_3OD}$ 3.2–4.0m4H, 3.84s2H, 4.68d(5Hz)1H, 5.98d (5Hz)1H, 6.9–7m14H, 8.60s1H. [$\alpha$]$_D^{25}$ −416° (c=0.546, CHCl$_3$+CH$_3$OH(1:1)).

2. methyl 3-[4,4-(3-oxapentamethylene)guanylhydrazono]methyl-7-phthalimido-3-cephem-4-carboxylate, m.p. 247°–252° C (decomp.). IR: $\nu_{max}^{Nujol}$ 3480, 3365, 1800, 1770, 1716, 1600, 1575 cm$^{-1}$. UV: $\lambda_{max}^{EtOH}$ 220; 384nm (saturated solution in ethanol).

3. diphenylmethyl 3-(4-nitroguanylhydrazono)methyl-7-(2-thienylacetamido)-3-cephem-4-carboxylate monohydrate, m.p. 156°–168° C (decomp.). IR: $\nu_{max}^{Nujol}$ 3440, 3306, 1786, 1722, 1670, 1620, 1565 cm$^{-1}$. UV: $\lambda_{max}^{EtOH}$ 350nm ($\epsilon$=33900). NMR: $\delta^{d-DMSO}$ (60 MHz) 3.80s2H, 5.28d(5Hz)1H, 5.90m1H, 6.8–7.7m14H, 8.30s1H, 8.7m3H, 9.17d(8Hz)1H. [$\alpha$]$_D^{24.5}$ −65.20 (immediately after dissolving); −45° (after 1 hour) (c=0.491 CHCl$_3$).

4. p-nitrobenzyl 3-[4,4-(3-oxapentamethylene)-guanylhydrazono]methyl-7-acetamido-3-cephem-4-carboxylate, m.p. 226°–231° C (decomp.). IR: $\nu_{max}^{Nujol}$ 3457, 3770, 3260, 1781, 1706, 1650, 1609, 1585, 1565, 1528, 1468 cm$^{-1}$. UV: $\lambda_{max}^{EtOH}$ 262; 378nm. NMR: $\delta^{d_6-DMSO}$ (60 MHz) 1.93s3H, 3.53br-s2H, 4.07ABq(47;18Hz)2H, 5.19d(5Hz)1H, 5.41s2H, 5.70q(8.5;5Hz)1H, 6.40br-s2H, 7.69d(9Hz) 2H, 8.23d(9Hz)2H, 8.25s1H, 8.82d(8.5Hz)1H.

5. p-nitrobenzyl 3-[4,4-(3-oxapentamethylene)-guanylhydrazono]-methyl-7-tertiary butoxycarbonylamino-3-cephem-4-carboxylate, m.p. 180°–188° C (decomp.). IR: $\nu_{max}^{CHCl}$ 3435, 3300, 3175, 1797, 1728, 1650, 1609, 1500, 1350 cm$^{-1}$. UV: $\lambda_{max}^{EtOH}$ 266nm ($\epsilon$=13400); 330nm ($\epsilon$=18200). NMR: $\delta^{d_6-DMSO}$ (60 MHz) 1.41s9H, 3.2–3.8br10H, 5.22d(5Hz)1H, 5.46brs2H, 5.4–5.7-1H, 7.70d(8Hz)Lb 2H, 8.02br2H, 5.24d(8Hz)2H, 8.52br-s1H.

EXAMPLE I-2.

To a solution of a 3-formyl-7-acylamino-3-cephem-4-carboxylic acid hemiacetal lactone (II) in an organic solvent is added a solution of a guanylhydrazine (III) and acid or a salt of the guanylhydrazine (III) in water, and let react at room temperature. The reaction mixture is concentrated to give crystals which are collected by filtration, washed with water and ethyl acetate or ether, and dried to give the objective cephalosporin compound (I). When the concentration of reaction mixture does not give solid product, or when the obtained solid is in small amount, the reaction mixture or washed solution is extracted with ethyl acetate, and the extract solution is washed with water, dried, and evaporated to give residue. Stirring of the residue in ether or petroleum ether gives desired cephalosporin compound (I).

The following Tables show the reaction conditions and the physical constants of the products. In the Tables, THF is for tetrahydrofuran, and ON is for overnight.

TABLE 1

$$\text{Acyl-NH—[β-lactam-S]—CHOH—CO—O (II)} \xrightarrow[\text{room temperature}]{H_2Z \text{ (III)}} \text{Acyl-NH—[β-lactam-S]—CH=Z, COOH (I)}$$

| Reaction No. | Acyl (II) | (mg) | =Z (III) | (mg) | Solvent (ml) | Time (hr) | Crop (mg) | (I) Yield (%) | No. |
|---|---|---|---|---|---|---|---|---|---|
| 1 | thienyl-CH$_2$CO— | (141) | =NN=C—NH$_2$, NH$_2$H$_2$SO$_4$ | (74) ½ | THF+H$_2$O 12+5 | 16 | 117 | 72 | 1 |
| 2 | thienyl-CH$_2$CO— | (211) | =NN=C—NH$_3$Br, NHCH$_3$ | (111) | THF+H$_2$O 11+3.5 | 16 | 147 | 58 | 2 |
| 3 | thienyl-CH$_2$CO— | (141) | =NN=C—NH$_2$HBr, N(CH$_3$)$_2$ | (146) | THF+H$_2$O 4+1 | 12 | 106 | 60.5 | 3 |
| 4 | thienyl-CH$_2$CO— | (141) | =NN=C—NH$_2$·HI, NHC$_2$H$_5$ | (221) | THF+H$_2$O 3.5+0.8 | 8.5 | 128 | 73 | 4 |
| 5 | thienyl-CH$_2$CO— | (141) | =NN=C—NH$_2$·HI, N(C$_2$H$_5$)$_2$ | (155) | THF+H$_2$O 12+4 | ON | 129 | 69.5 | 5 |
| 6 | thienyl-CH$_2$CO— | (142) | =NN=C—NHC$_2$H$_5$·HI, N(C$_2$H$_5$)$_2$ | (240) | THF+H$_2$O 2.8+1 | ON | 157 | 71 | 6 |
| 7 | thienyl-CH$_2$CO— | (141) | =NN=C—NH$_2$, NHCH$_2$CH=CH$_2$·HBr | (234) | THF+H$_2$O 7+1.5 | 17 | 131 | 73 | 7 |
| 8 | thienyl-CH$_2$CO— | (142) | =NN=C—NHCH$_3$·HI, NHCH$_2$CH=CH$_2$ | (154) | THF+H$_2$O 2.8+1 | ON | 153 | 73 | 8 |
| 9 | thienyl-CH$_2$CO— | (141) | =NN=C—NH$_2$·HI, N(CH$_2$CH=CH$_2$)$_2$ | (226) | THF+H$_2$O 12+4 | ON | 124 | 63.5 | 9 |
| 10 | thienyl-CH$_2$CO— | (141) | =NN=C—NH$_2$, NHCH$_2$C$_6$H$_5$·HBr | (147) | THF+H$_2$O 7+1.5 | 22 | 176 | 81 | 10 |
| 11 | thienyl-CH$_2$CO— | (142) | =NN=C—NHCH$_3$·HI, N(CH$_2$C$_6$H$_5$)$_2$ | (238) | THF+H$_2$O 2.8+1 | ON | 294 | 100 | 11 |
| 12 | thienyl-CH$_2$CO— | (176) | =NN=C—NH$_2$·HI, NHC$_6$H$_5$ | (297) | THF+H$_2$O 3.5+1 | 7 | 216 | 80 | 12 |
| 13 | thienyl-CH$_2$CO— | (176) | =NN=C—NH$_2$·HI, NH—C$_6$H$_4$—OCH$_3$ | (231) | THF+H$_2$O 3.5+1 | 17 | 230 | 81.6 | 13 |
| 14 | thienyl-CH$_2$CO— | (176) | =NN=C—NH$_2$·HI, NH—C$_6$H$_4$—COOCH$_3$ | (250) | THF+H$_2$O 3.5+1 | 20.5 | 256 | 80.5 | 14 |

TABLE 1-continued $$\text{Acyl-NH} \begin{array}{c} \text{(II)} \end{array} \xrightarrow[\text{room temperature}]{H_2Z \text{ (III)}} \text{Acyl-NH} \begin{array}{c} \text{(I)} \end{array}$$

| Reaction No. | (II) Acyl | (mg) | (III) =Z | (mg) | Solvent (ml) | Time (hr) | Crop (mg) | (I) Yield (%) | No. |
|---|---|---|---|---|---|---|---|---|---|
| 15 | thienyl-CH₂CO— | (352.3) | =NN=C(NH₂)-N(CH₃)(C₆H₅)·HI | (440) | THF+H₂O 20+2 | ON | 360 | 67 | 15 |
| 16 | thienyl-CH₂CO— | (141) | =NN=C(NH₂)-NHNH₂·HCl | (50.2) | THF+H₂O 7+1.7 | 18 | 131 | 77.5 | 16 |
| 17 | thienyl-CH₂CO— | (211) | =NN=C(NHCH₃)-NHNH₂·HI | (152) | THF+H₂O 11+3.5 | 16 | 171 | 65 | 17 |
| 18 | thienyl-CH₂CO— | (211) | =NN=C(CH₃NNH₂)-NH₂·HBr | (121) | THF+H₂O 21+6 | 19 | 189 | 67 | 18 |
| 19 | thienyl-CH₂CO— | (141) | =NN=C(NHCH₃)-NNHCOCH₃·HI | (164) | THF+H₂O 8+2 | 40 | 135 | 71 | 19 |
| 20 | thienyl-CH₂CO— | (141) | =NN=C(NHOH)-NH₂·HI | (126) | THF+H₂O 7+1.5 | 20 | 118 | 69.4 | 20 |
| 21 | thienyl-CH₂CO— | (141) | =NN=C(NHOCH₃)-NH₂·HI | (168) | THF+H₂O 3.5+0.8 | 8.5 | 118 | 67.2 | 21 |
| 22 | thienyl-CH₂CO— | (211) | =NN=C(NHNO₂)-NH₂+HCl | (107) | THF+H₂O 20+5.9 | 6 | 242 | 89 | 22 |
| 23 | thienyl-CH₂CO— | (211) | =NN=C(pyrrolidinyl)-NH₂·HBr | (188) | THF+H₂O 13+2.5 | 13 | 162 | 58 | 23 |
| 24 | thienyl-CH₂CO— | (176) | =NN=C(piperidinyl)-NH₂·HI | (202) | THF+H₂O 3.5+1 | 20 | 178 | 64.2 | 24 |
| 25 | thienyl-CH₂CO— | (282) | =NN=C(pyrrolidinyl)-NH·HI | (286) | THF+H₂O 24+8 | ON | 225 | 57.7 | 25 |
| 26 | thienyl-CH₂CO— | (352.3) | =NN=C(tetrahydropyridinyl)-NH₂ | (402.3) | THF+H₂O 20+2 | ON | 435 | 80 | 26 |

TABLE 1-continued $$\underset{(II)}{\text{Acyl-NH} \diagup \text{S} \diagdown \text{CHOH}} \xrightarrow[\text{room temperature}]{\text{H}_2\text{Z (III)}} \underset{(I)}{\text{Acyl-NH} \diagup \text{S} \diagdown \text{CH}=\text{Z}}$$

| Reaction No. | Acyl (II) | (mg) | =Z (III) | (mg) | Solvent (ml) | Time (hr) | Crop (mg) | (I) Yield (%) | No. |
|---|---|---|---|---|---|---|---|---|---|
| 27 | thiophene-CH₂CO— | (352.3) | =NN≡C—NH₂·HI, piperidine-N | (425) | THF+H₂O 20+2 | ON | 588 | 99.0 | 27 |
| 28 | thiophene-CH₂CO— | (440) | =NN≡C—morpholine, NH₂·HBr | (563) | THF+H₂O 11+3 | 16 | 412 | 60 | 28 |
| 29 | thiophene-CH₂CO— | (1000) | =NN≡C—piperidine, NH₂·HBr | (958.5) | THF+H₂O 15+4 | 17 | 895 | 65 | 29 |
| 30 | thiophene-CH₂CO— | (704) | =NN≡C—morpholine·HI, NH₂ | (768) | THF+H₂O 16+3 | 40 | 683 | 61 | 30 |
| 31 | thiophene-CH₂CO— | (142) | =NN≡C—morpholine·HI, NHC₂H₅ | (250) | THF+H₂O 2.8+1 | 4 | 148 | 65 | 31 |
| 32 | thiophene-CH₂CO— | (70.5) | =NN≡C—NH₂, 2-methylmorpholine | (143) | THF+H₂O 2.8+0.7 | 16 | 74 | 68.4 | 32 |
| 33 | thiophene-CH₂CO— | (105.7) | =NN≡C—NH₂·HI, 3-methylmorpholine | (129) | THF+H₂O 4.2+1.1 | 14.5 | 118 | 68.4 | 33 |
| 34 | thiophene-CH₂CO— | (105.7) | =NN≡C—NH₂·HI, 3,5-dimethylmorpholine | (135) | THF+H₂O 4.2+1.1 | 20.5 | 128 | 72.5 | 34 |
| 35 | thiophene-CH₂CO— | (141) | =NN≡C—2,6-dimethylmorpholine, NH₂·HI | (135) | THF+H₂O 3+0.3 | 15 | 94 | 62 | 35 |
| 36 | thiophene-CH₂CO— | (189) | =NN≡C—N(tetrahydrooxazine), NH₂·HI | (365) | THF+H₂O 7.5+2 | 16 | 232 | 77.1 | 36 |

TABLE 1-continued

Acyl-NH—[β-lactam-S]—CHOH-CO-O (II) + H₂Z (III) →(room temperature)→ Acyl-NH—[β-lactam-S]—CH=Z, COOH (I)

| Reaction No. | (II) Acyl | (mg) | =Z (III) | (mg) | Solvent (ml) | Time (hr) | Crop (mg) | (I) Yield (%) | No. |
|---|---|---|---|---|---|---|---|---|---|
| 37 | thiophene-CH$_2$CO— | (106) | =NNH—C(=NH)—N(tetrahydrooxazine). HI | (163) | THF+H$_2$O 4.2+1.1 | 16 | 125 | 75.5 | 37 |
| 38 | thiophene-CH$_2$CO— | (141) | =NN=C—NH$_2$ HI, N(thiazolidine) | (164) | THP+H$_2$O 12+4 | ON | 170 | 75.5 | 38 |
| 39 | thiophene-CH$_2$CO— | (141) | =NN=C—NH$_2$. HI, N(thiazinane) | (172) | THF+H | | 75 | | 39 |
| 40 | thiophene-CH$_2$CO— | (352) | =NNH—(imidazoline). 2H$_2$O | | THF+H$_2$O 20+2 | ON | 238 | 46.3 | 40 |
| 41 | thiophene-CH$_2$CO— | (200) | =NNH—(imidazolinone). HI | (277) | THF+H$_2$O 17+6 | ON | 190 | 74.5 | 41 |
| 42 | H— | (69) | =NN=C—N(morpholine), NH$_2$. HBr | (100) | THF+H$_2$O 4+1 | 5 | 42 | 40 | 42 |
| 43 | C$_6$H$_5$OCH$_2$CO— | (36) | =NN=C—N(morpholine), NH$_2$. HBr | (34) | THF+H$_2$O 2+0.5 | 28 | 25 | 50 | 43 |
| 44 | CH$_3$—N(tetrazole)—S—CH$_2$CO— | (19.2) | =NN=C—NH$_2$, N(morpholine). HBr | (20.9) | THF+H$_2$O 2+0.4 | 21 | 10 | 35.1 | 44 |
| 45 | C$_6$H$_5$CH(NH$_2$)CO— | (35) | =NN=C—N(morpholine), NH$_2$. HBr | (34) | THF+H$_2$O 1+1 | 15 | 40 | 85 | 45 |
| 46 | C$_6$H$_5$CH(NHCOO-tert-C$_4$H$_9$)CO— | (139) | =NN=C—N(morpholine), NH$_2$. HBr | (135) | THF+H$_2$O 5.6+1.4 | 24 | 68 | 39 | 46 |
| 47 | C$_6$H$_5$CH$_2$CO— | (35) | =NN=C—N(morpholine), NH$_2$. HBr | (34) | THF+H$_2$O 2+0.5 | 28 | 19 | 41 | 47 |

TABLE 1-continued $$\text{Acyl-NH} \underset{(II)}{\overset{S}{\underset{CO-O}{\bigcirc}}} \text{CHOH} \xrightarrow[\text{room temperature}]{H_2Z \text{ (III)}} \text{Acyl-NH} \underset{(I)}{\overset{S}{\underset{COOH}{\bigcirc}}} CH=Z$$

| Reaction No. | Acyl (II) | (mg) | =Z (III) | (mg) | Solvent (ml) | Time (hr) | Crop (mg) | (I) Yield (%) | No. |
|---|---|---|---|---|---|---|---|---|---|
| 48 | furyl-CH₂CO— | (67.3) | =NN=C(NH₂)-morpholino · HBr | (68) | THF+H₂O 2.8+0.7 | 23 | 58.5 | 58.2 | 48 |
| 49 | thienyl-CH₂CO— | (70.5) | =NN=C(NH₂)-morpholino · HBr | (68) | THF+H₂O 2.8+0.7 | 23 | 66 | 63 | 49 |
| 50 | tetrazolyl-CH₂CO— | (101) | =NN=C(NH₂)-morpholino · HBr | (135) | THF+H₂O 5+2— | ON | 93 | 67 | 50 |
| 51 | (CH₃)₃C—OCO— | (30) | =NN—C(NH₂·HBr)-morpholino | (31) | THF+H₂O 1.2+0.3 | 29 | 17 | 41 | 51 |
| 52 | Cl₃CCH₂OCO— | (101) | =NN—C(NH₂·HBr)-morpholino | (84) | THF+H₂O 4+1 | 19 | 96 | 73 | 52 |
| 53 | 2-NO₂-C₆H₄-S— (7α — CH₃O Derivative) | (38) | =NN—C(NH₂·HBr)-morpholino | (34) | THF+H₂O 1.5+0.4 | 21 | 27 | 54 | 53 |
| 54 | thienyl-CH₂CO— (R=CH₃) | (38.2) | =NN—C(NH₂·HBr)-morpholino | (33.7) | THF+H₂O 5+1.25 | ON | 27 | 53 | 54 |
| 55 | thienyl-CH₂CO— | (36.6) | =NN—C(NH₂)—NHNO₂ + HCl | (18) | THF+H₂O 2+0.5 | 5 | 30 | 64 | 55 |
| 56 | thienyl-CH₂CO— | (180.9) | =NN—C(H₂N)(CH₃)—NOH HBr | (190) | THF+H₂O 7.2+1.8 | 19 | 99 | 42.3 | 56 |
| 57 | thienyl-CH₂CO— | (105.7) | =NN—C(H₂N)(CH₃)—NOCH₃ | (123) | THF+H₂O 4.2+1.1 | 21.5 | 98 | 61 | 57 |
| 58 | thienyl-CH₂CO— | (142) | =NN—C(=N-NH-C(=S)-NH—)—NNH₂HCl | (88) | THF+H₂O 14+7.3 | ON | 138 | 77 | 58 |

TABLE II

Structure: Acyl-NH on β-lactam fused with thiazine ring, CH=Z substituent, COOH group.

| Compound No. | Acyl | =Z | m.p. | IR: $\nu_{max}^{Nujol}$ cm$^{-1}$ | UV: $\lambda_{max}^{EtOH}$ nm($\epsilon$) |
|---|---|---|---|---|---|
| 1 | 2-thienyl-CH$_2$CO— | =NN=C(NH$_2$)(NH$_2$) | 208–213° C (dec.) | 3465,3265,1792, 1772,1665,1625, 1535. | 233(14000), 321(23200). (CH$_3$OH) |
| 2 | 2-thienyl-CH$_2$CO— | =NN=C(NH$_2$)(HNCH$_3$) 1/2HBr H$_2$O | 190–196° C (dec.) | 3260,3200,1770, 1660,1635,1536. | 234(13800), 319(26300). |
| 3 | 2-thienyl-CH$_2$CO— | =NN=C(NH$_2$)(N(CH$_3$)$_2$) HBr 1/2H$_2$O | 187–195° C (dec.) | 3400,3275,3183, 1798,1781,1722, 1661,1613,1543, 1522. | 234(13900), 319(31600). |
| 4 | 2-thienyl-CH$_2$CO— | =NN=C(NH$_2$)(NHC$_2$H$_5$) | 175–186° C (dec.) | 3276,3200,1778, 1670,1628,1537. | 225(13500), 320(22100). |
| 5 | 2-thienyl-CH$_2$CO— | =NN=C(NH$_2$)(N(C$_2$H$_5$)$_2$) HI | 169–172° C (dec.) | 3250,3130,1781, 1647,1603,1528. | 225(15600), 320(19500). |
| 6 | 2-thienyl-CH$_2$CO— | =NN=C(NHC$_2$H$_5$)(N(C$_2$H$_5$)$_2$) 1/2HI | 165–170° C (dec.) | 3260,1785,1625, 1595,1530. | 223(22100), 325(24800). |
| 7 | 2-thienyl-CH$_2$CO— | =NN=C(NH$_2$)(NHCH$_2$CH=CH$_2$) 1/2HBr | 181–185° C (dec.) | 3266,3176,1775, 1665,1625,1533. | 234(12300), 319(23900). |
| 8 | 2-thienyl-CH$_2$CO— | =NN=C(NHCH$_3$)(NHCH$_2$CH=CH$_2$) 1/22HI H$_2$O | 170–175° C (dec.) | 3230,1780,1655, 1611,1516. | 223(20100), 320(25800). |
| 9 | 2-thienyl-CH$_2$CO— | =NN=C(NH$_2$)(N(CH$_2$CH=CH$_2$)$_2$) | 155–165° C (dec.) | 3270,3190,1783, 1648,1635,1600, 1535. | 225(17900), 321(22900). |
| 10 | 2-thienyl-CH$_2$CO— | =NN=C(NH$_2$)(NHCH$_2$C$_6$H$_5$) 1/2 HBr | 177–181° C (dec.) | 3260,3171,1780, 1664,1630,1535, 1500. | 233(14900), 319(26800). |
| 11 | 2-thienyl-CH$_2$CO— | —NN=C(NHCH$_3$)(N(CH$_2$C$_6$H$_5$)$_2$) 1/2HI | 169–175° C (dec.) | 3175,1785,1660, 1625,1595,1495. | 327(28500). |
| 12 | 2-thienyl-CH$_2$CO— | =NN=C(NH$_2$)(NHC$_6$H$_5$) 5/2H$_2$O | 183–188° C (dec.) | 3260,1777,1661, 1595,1532. | 225(17800), 322(24700). |
| 13 | 2-thienyl-CH$_2$CO— | =NN=C(NH$_2$)(NH-C$_6$H$_4$-OCH$_3$) 1/4HI H$_2$O | 183–186° C (dec.) | 3285,3190,1775, 1660,1619,1514. | 224(23100), 324(27300). |
| 14 | 2-thienyl-CH$_2$CO— | =NN=C(NH$_2$)(NH-C$_6$H$_4$-COOCH$_3$) 1/3HI H$_2$O | 178–184° C (dec.) | 3280,1778,1715, 1662,1601,1535, 1515. | 328(28200). |

TABLE II-continued

| No. | Acyl | =CH-Z group | m.p. | IR | UV |
|---|---|---|---|---|---|
| 15 | thiophene-2-CH₂CO— | =NN=C(NH₂)(CH₃NC₆H₅) | 190–195° C (dec.) | 3280,1780,1643, 1608,1590. | 225(19100), 324(25300). |
| 16 | thiophene-2-CH₂CO— | =NN=C(NHNH₂)(HCl NH₂) | 203–208° C (dec.) | 3476,3276,1770, 1665,1600,1535. | 235(satd. soln) 326 |
| 17 | thiophene-2-CH₂CO— | =NN=C(NHNH₂)(NHCH₃) | 197–203° C (dec.) | 3230,1775,1665, 1630,1600,1527. | 224(17400), 322(21600). |
| 18 | thiophene-2-CH₂CO— | =NN=C(NH₂)(CH₃NNH₂) | 182–193° C (dec.) | 3200,1777,1677, 1630,1597,1540. | 234(10100), 322(15800). |
| 19 | thiophene-2-CH₂CO— | =NH=C(NNHCOCH₃)(NHCH₃) | 184–191° C (dec.) | 3500,3260,3205, 1,808,1774,1680 1666,1612,1542, 1517. | 224(satd. soln) 322 |
| 20 | thiophene-2-CH₂CO— | =NN=C(NH₂)(NHOH)·H₂O | 181–191° C (dec.) | 3490,3357,3275, 1757,1652,1623, 1532. | 231(sat soln) 320 |
| 21 | thiophene-2-CH₂CO— | =NH=C(NH₂)(NHOCH₃) | 173–188° C (dec.) | 3278,3198,1777, 1657,1630,1600, 1537. | 224(13800), 321(20500). |
| 22 | thiophene-2-CH₂CO— | =NN=C(NHNO₂)(NH₂) | 180–188° C (dec.) | 3425,3280,1773, 1715,1660,1627, 1595,1570,1535. | 234(13800), 266(7900), 348(34000). |
| 23 | thiophene-2-CH₂CO— | =NN=C(pyrrolidinyl)(NH₂) | 221–224° C (dec.) | 3435,3262,3185, 1775,1663,1605, 1544. | 235(13700), 320(29000). |
| 24 | thiophene-2-CH₂CO— | =NN=C(NH₂)(piperidinyl) | 195–198° C (dec.) | 3280,3190,1781, 1655,1605,1537. | 225(19500), 322(30700). |
| 25 | thiophene-2-CH₂CO— | =NN=C(pyrrolyl)(NH₂) | 203–205° C (dec.) | 3265,3205,1777, 1667,1600,1550. | 235(satd. soln) 319 |
| 26 | thiophene-2-CH₂CO— | =NN=C(NH₂)(tetrahydropyridinyl) | 207–209° C (dec.) | 3250,3190,1778, 1655,1605. | 224(18400), 321(29500). |
| 27 | thiophene-2-CH₂CO— | =NN=C(NH₂)(piperidinyl) | 186–188° C (dec.) | 3260,3180,1779, 1647,1603,1534. | 223(20700), 323(24000). |

TABLE II-continued

| | Acyl | =CH-Z group | m.p. | IR | UV |
|---|---|---|---|---|---|
| 28 | thiophene-2-CH₂CO— | =NN=C(NH₂)-N(morpholino) · 1/2HBr · 2H₂O | 226–228° C (dec.) | 3387,3252,3200, 1780,1665,1618, 1535,1492. | 235(16200) 321(33200). |
| 29 | thiophene-2-CH₂CO— | =NN=C(NH₂)-N(morpholino) · 1/2H₂O | 215–217° C (dec.) | 3500,2000,1781, 1678,1643,1597, 1536. | — |
| 30 | thiophene-2-CH₂CO— | =NN=C(NH₂)-N(morpholino) · 1/2HI | 223–225° C (dec.) | 3386,3261,3200, 1535. | 226(18000), 321(3200). |
| 31 | thiophene-2-CH₂CO— | =NN=C(NHC₂H₅)-N(morpholino) · 1/2HI · H₂O | 181–185° C (dec.) | 3230,1780,1665, 1630,1600. | 227(20500), 325(26700). |
| 32 | thiophene-2-CH₂CO— | =NN=C(NH₂)-N(2-methylmorpholino) · 1/2HBr · 1/2H₂O | 190–196° C (dec.) | 3266,3186,1781, 1657,1609,1535. | 235(19400), 322(28000). |
| 33 | thiophene-2-CH₂CO— | =NN=C(NH₂)-N(3-methylmorpholino) | 192–197° C (dec.) | 3400,3258,3183, 1784,1641,1603, 1529. | 223(21400), 322(29900). |
| 34 | thiophene-2-CH₂CO— | =NN=C(NH₂)-N(3,5-dimethylmorpholino) | 190–195° C (dec.) | 3380,3260,3180, 1783,1641,1601, 1533. | 224(20400), 322(29600). |
| 35 | thiophene-2-CH₂CO— | =NN=C(NH₂)-N(2,6-dimethylmorpholino) · H₂O | 204–206° C (dec.) | 3520,3290,1803, 1672,1662,1622, 1590,1540. | 234(15600), 323(30600). |
| 36 | thiophene-2-CH₂CO— | =NN=C(NH₂)-N(1,3-oxazinan-3-yl) | 185–190° C (dec.) | 3265,3205,1780, 1653,1609,1533. | 224(19600), 327(23800). |
| 37 | thiophene-2-CH₂CO— | =NN=C(NH₂)-N(1,4-oxazinan-4-yl) | 192–195° C (dec.) | 3255,1780,1648, 1609,1533. | 224(18500), 322(25500). |
| 38 | thiophene-2-CH₂CO— | =NN=C(NH₂)-N(thiazolidin-3-yl) | 187–190° C (dec.) | 3260,3170,1775, 1646,1604,1532. | 225 (satd. soln.) 323 |
| 39 | thiophene-2-CH₂CO— | =NN=C(NH₂)-N(thiomorpholino) | 185–188° C (dec.) | 3245,1774,1662, 1645,1603,1535. | 224(17600), 322(26600). |
| 40 | thiophene-2-CH₂CO— | =NNH-C(=N-imidazolin-2-yl)NH · 1/3HI · 2H₂O | 194–198° C (dec.) | 3245,1774,1662, 1610,1530. | 266(18300), 318(26000). |

TABLE II-continued

| | Acyl | =CH=Z group | m.p. | IR | UV |
|---|---|---|---|---|---|
| 41 | 2-thienyl-CH₂CO— | =NNH-C(=NH)-NH (imidazolinone) | 184–190° C | 3240,1778,1690, 1598,1528. | 233(14000) 327(17000). |
| 42 | H— | =NN=C(NH₂)-N(morpholino) · 2F₃CCOOH | 230–250° C (dec.) | 3323,3180,1786, 1661,1611,1547, 1453. | 323(18500). |
| 43 | C₆H₅OCH₂CO— | =NN=C(NH₂)-N(morpholino) | 175–185° C (dec.) | 3405,3310,1782, 1705,1665,1615. | 322(20700). |
| 44 | 1-methyl-tetrazol-5-yl-S-CH₂CO— | =NN=C(NH₂)-N(morpholino) | 189–192° C (dec.) | 3265,1780,1655, 1613,1552. | 320(32200). |
| 45 | C₆H₅CH(NH₂)CO— · CF₃COOH | =NN=C(NH₂)-N(morpholino) | 225–235° C (dec.) | 3320,3195,1789, 1675,1619,1552. | 324(17700). |
| 46 | C₆H₅CH(NHCOO-tert-C₄H₉)CO— | =NN=C(NH₂)-N(morpholino) | 227–235° C (dec.) | 3320,1791,1696, 1664,1619,1522, 1497,1457. | 322(20600). |
| 47 | C₆H₅CH₂CO— | =NN=C(NH₂)-N(morpholino) · 1/2HBr | 232–236° C (dec.) | 3270,1785,1664, 1622,1532. | 321(28400). |
| 48 | 2-furyl-CH₂CO— | =NN=C(NH₂)-N(morpholino) · HBr · 2H₂O | 200–208° C (dec.) | 3380,3270,1779, 1664,1604,1543, 1507. | 323(29000). |
| 49 | 2-thienyl-CH₂CO— | =NN=C(NH₂)-N(morpholino) | 200–210° C (dec.) | 3165,1776,1655, 1606,1532. | 231(14000), 321(28000). |
| 50 | 1H-tetrazol-1-yl-CH₂CO— | =NN=C(NH₂)-N(morpholino) · HBr | 193–196° C (dec.) | 3310,3210,1779, 1735,1685,1650, 1605. | 328(17900). |
| 51 | (CH₃)₃C—OCO— | =NN=C(NH₂)-N(morpholino) | 227–235° C (dec.) | 3322,1779,1698, 1652,1605,1519, 1407. | 321(22500). |
| 52 | Cl₃CCH₂OCO— | =NN=C(NH₂)-N(morpholino) | 200–212° C | 3305,3205,1788, 1733,1651,1614, 1537,1460. | 323(18100). |
| 53 | 2-(o-nitrophenylthio)— | =NN=C(NH₂)-N(morpholino) | 195–262° C (dec.) | 3380,3185,1781, 1669,1632,1592, 1513,1457. | 243 satd. 329 soln. |
| 54 | (7α—CH₃O derivative) 2-thienyl-CH₂CO— | =NN=C(NH₂)-N(morpholino) | 180–184° C (dec.) | 3310,3190,1779, 1648,1612. | 234(13900), 322(23800). |

TABLE II-continued

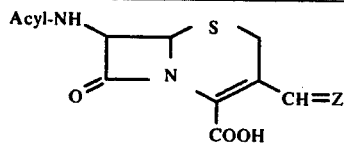

| No. | Acyl | =Z | m.p. | IR | UV |
|---|---|---|---|---|---|
| 55 | (R = CH₃) [thiophene-CH₂CO—] | =NN=C(NH₂)NHNO₂ | 170–185° C (dec.) | 3325,3250,1803, 1739,1690,1620, 1525. | 239(14100), 267(12000). |
| 56 | thiophene-CH₂CO— | =NN=C(NH₂)(CH₃)—NOH | 183–187° C (dec.) | 3450,3270,3205, 1779,1664,1614, 1578,1540. | 235(15200), 335(23400). in 0.01123N Na₂CO₃ |
| 57 | thiophene-CH₂CO— | =NN=C(NH₂)(CH₃)—NOCH₃ | 187–191° C (dec.) | 3246,1779,1663, 1632,1532. | 225(18200), 318(2300). |
| 58 | thiophene-CH₂CO— | =NN=C—NNH₂ (triazole-thione) | 220–235° C (dec.) | 3260,1780,1717, 1667,1640,1550, 1495. | 240(16700), 262(15800), 336(20800). |

| Compound No. | Acyl | =Z | NMR: δ d₆-DMSO (60 MHz) (Values in ( ) show coupling consts.) | [α]$_D^{t°C}$ (c) |
|---|---|---|---|---|
| 1 | thiophene-CH₂CO— | =NN=C(NH₂)NH₂ | 3.80s2H,3.90ABq(40;18Hz)2H, 5.14d(5Hz)1H,5.62dd(8;5Hz)1H, 6.7–7.5m3H,9.08d(8Hz)1H,9.33s 1H. | +257.2° 0.445DMSO 24.5°C |
| 2 | thiophene-CH₂CO— | =NN=C(NH₂)(HNCH₃) 1/2HBr · H₂O | 2.85br-s3H,3.80s2H,5.17d(5Hz) 1H,5.68dd(8;5Hz)1H,6.78–7.55m 3H,8.95s1H,9.10d(8Hz)1H. | +80.6° 0.304DMSO 24°C |
| 3 | thiophene-CH₂CO— | =NN=C(NH₂)N(CH₃)₂ HBr 1/2H₂O | 3.08s6H,3.82s2H,3.93ABq(58.5; 18.5Hz)2H,5.17d(5Hz)1H,5.72dd (8;5Hz)1H,6.80–7.50m3H,7.83 br-s2H,8.60s1H,9.15d(8Hz)1H. | −267.3° 0.314DMSO 23°C |
| 4 | thiophene-CH₂CO— | =NN=C(NH₂)NHC₂H₅ | 1.15t(7Hz)2H,3.78s2H,5.15d(5 Hz)1H,5.67dd(8;5Hz)1H,6.75–6.75– 7.50m3H,8.17brs1H,8.88s1H,9.08 d(8Hz)1H. | +45.6° 0.296DMSO 21°C |
| 5 | thiophene-CH₂CO— | =NN=C(NH₂)N(C₂H₅)₂ HI | 3.83s2H,5.17d(5Hz)1H,5.73dd(8; 5Hz)1H,6.8–7.5m3H,8.58s1H,9.28 d(8Hz)1H. | −159.1° 0.403DMSO 24.5°C |
| 6 | thiophene-CH₂CO— | =NN=C(NHC₂H₅)N(C₂H₅)₂ 1/2HI | 1.15m9H,5.12m1H,5.62m1H,6.75– 7.47m3H,7.87br1H,8.63s1H,9.12m 1H. | −159° 0.314DMSO 22.5°C |
| 7 | thiophene-CH₂CO— | =NN=C(NH₂)NHCH₂CH=CH₂ 1/2HBr | 3.78s2H,3.83–5.42m7H,6.75–7.50 m3H,8.23brs2H,8.98s1H,9.12d(8 Hz)1H. | +79.3° 0.323DMSO 21°C |
| 8 | thiophene-CH₂CO— | =NN=C(NHCH₃)NHCH₂CH=CH₂ 1/22HI H₂O | 2.90brs3H,3.80s2H,4.95–5.52m 3H,5.52–6.03m2H,6.75–7.50m5H, 8.63s1H,9.13d(8Hz)1H. | −238° 0.290DMSO 22.5°C |
| 9 | thiophene-CH₂CO— | =NN=C(NH₂)N(CH₂CH=CH₂)₂ | 3.79s2H,6.8–7.5m3H,7.88brs1H, 8.58s1H,9.10d(8;5Hz)1H. | −169.9° 0.332DMSO 24.0°C |
| 10 | thiophene-CH₂CO— | =NN=C(NH₂)NHCH₂C₆H₅ 1/2HBr | 3.78s2H,5.15d(5Hz)1H,5.65dd(8; 5Hz)1H,6.78–7.50m8H,8.98s1H, 9.13d(8Hz)1H. | +40.0° 0.333DMSO 24°C |
| 11 | thiophene-CH₂CO— | —NN=C(NHCH₃)N(CH₂C₆H₅)₂ 1/2HI | 2.90s3H,5.12m1H,5.67m1H,6.8– 7.5m13H,8.62s1H,9.13br1H. | −103° 0.300DMSO 21.0°C |

TABLE II-continued

| Compound No. | Acyl | =Z | NMR: δd₆-DMSO (60 MHz) (Values in ( ) show coupling consts.) | $[\alpha]_D^{t°C}$ (c) |
|---|---|---|---|---|
| 12 | thiophene-2-CH₂CO— | =NN=C(NH₂)(NHC₆H₅) 5/2H₂O | 3.80s2H,5.20d(5Hz)1H,5.70dd(8; 5Hz)1H,6.8–7.8m8H,9.17d(8Hz) 1H,9.25s1H. | +12.9° 0.459DMSO 21°C |
| 13 | thiophene-2-CH₂CO— | =NN=C(NH₂)(NH-C₆H₄-OCH₃) 1/4HI H₂O | 5.16d(5Hz)1H,5.63dd(8;5Hz)1H, 6.7–7.5m7H,9.12d(8Hz)1H,9.18 1H. | +61.0° 0.446DMSO 22°C |
| 14 | thiophene-2-CH₂CO— | =NN=C(NH₂)(NH-C₆H₄-COOCH₃) 1/3HI H₂O | — | −92.1° 0.515DMSO 23°C |
| 15 | thiophene-2-CH₂CO— | =NN=C(NH₂)(CH₃NC₆H₅) | — | −222.9° 0.498DMSO 25°C |
| 16 | thiophene-2-CH₂CO— | =NN=C(NHNH₂)(HCl NH₂) | 3.78s2H,5.15d(5Hz)1H,5.67dd/6(8; 5Hz)1H,6.75–7.50m3H,9.30d2H. | +67.4° 0.337DMSO 24°C |
| 17 | thiophene-2-CH₂OH— | —NH=C(NHNH₂)(NHCH₃) | 2.85br-s3H,3.78s2H,5.17d(5Hz) 1H,5.67dd(8;5Hz)1H,6.78–7.56m 3H,8.62s1H,9.13d(8Hz)1H. | −217.5° 0.323DMSO 24°C |
| 18 | thiophene-2-CH₂CO— | =NN=C(NH₂)(CH₃NNH₂) | 3.03br-s3H,3.78s2H,5.22d(5Hz) 1H,5.73dd(8;5Hz)1H,6.77–7.55m 3H,8.60s1H,9.17d(8Hz)1H. | −147.3° 0.316DMSO 24°C |
| 19 | thiophene-2-CH₂CO— | =NN=C(NNHCOCH₃)(NHCH₃) | 1.93s3H,2.90br-s3H,3.78s2H, 5.15d(5Hz)1H,5.65dd(8;5Hz)1H, 6.78–7.50m3H,8.70s1H,9.10d(8 Hz)1H. | −223.6° 0.102DMSO 26°C |
| 20 | thiophene-2-CH₂CO— | =NN=C(NH₂)(NHOH) H₂O | 3.78s2H,5.13d(5Hz)1H,5.65-1H, 6.75–7.5m3H,8.93H. | −31.9°(0 min.) +66.9°(10 mins.) 0.329DMSO 23.5°C |
| 21 | thiophene-2-CH₂CO— | =NN=C(NH₂)(NHOCH₃) | 3.72s3H,3.78s2H,5.15d(5Hz)1H, 5.68dd(8;5Hz)1H,6.75–7.5m3H, 8.85s1H,9.13d(8Hz)1H. | −59.1° 0.335DMSO 21°C |
| 22 | thiophene-2-CH₂CO— | =NN=C(NHNO₂)(NH₂) | 3.78s2H,3.52–4.55ABq(62;18Hz) 2H,5.22d(4Hz)1H,6.83–7.45m3H, 8.33s1H,8.38–8.88br1H,9.15d(8 Hz)1H,11.77br-s1H,5.95dd1H. | −301.7° 0.306MDSO 23°C |
| 23 | thiophene-2-CH₂CO— | =NN=C(pyrrolidinyl)(NH₂) | 1.92–3.42m4H,3.78s2H,5.13d(5 Hz)1H,5.63dd(8;5Hz)1H,6.80– 7.55m3H,7.60br-s2H,8.62H, 9.27d(8Hz)1H. | −462.9° 0.302DMSO 23°C |
| 24 | thiophene-2-CH₂CO— | =NN=C(NH₂)(piperidinyl) | 1.60brs6H,3.2–4.8m8H,5.07d(5 Hz)1H,5.62dd(8;5Hz)1H,6.8–7.5m 3H,8.55s1H,9.08d(8Hz)1H. | −341.3° 0.531DMSO 25.5°C |
| 25 | thiophene-2-CH₂CO— | =NN=C(pyrrolyl)(NH₂) | 3.78s2H,5.13d(9.5Hz)1H,5.94s 2H,6.8–7.5m3H,7.67br-s1H,8.68d 1H,9.11d(8Hz)1H. | −501.5° 0.494DMSO 25°C |

TABLE II-continued

| Compound No. | Acyl | =Z | NMR: δd₆-DMSO (60 MHz) (Values in ( ) show coupling consts.) | $[\alpha]_D^{t°C}$ (c) |
|---|---|---|---|---|
| 26 | thiophene-CH₂CO— | =NN=C(NH₂)-N (tetrahydropyridine) | 2.26brs2H,3.60brs2H,4.05brs2H, 5.14d(5Hz)1H,5.67brs1H,5.82brs 2H,6.78–7.5m3H,7.90brs2H,8.63 s1H,9.11d(7Hz)1H. | −328.7° 0.547DMSO 25.0° C |
| 27 | thiophene-CH₂CO— | =NN=C(NH₂)-N (piperidine) | 1.55brs8H,5.15d(5Hz)1H,5.70brs 1H,6.82–7.58m3H,7.80brs2H,8.60 s1H,9.15d(8Hz)1H. | −189.5° 0.502DMSO 25.0° C |
| 28 | thiophene-CH₂CO— | =NN=C(NH₂)-N(morpholine) 1/2HBr 2H₂O | 3.63br-s8H,3.77s2H,3.92ABq(58; 18Hz)2H,5.13d(5Hz)1H,5.07dd(8; 5Hz)1H,6.78–78.7–7.5m3H,7.95br-2H, 8.57s1H,9.08d(8Hz)1H. | −361.1° 0.308DMSO 23° C |
| 29 | thiophene-CH₂CO— | =NN=C(NH₂)-N(morpholine) 1/2H₂O | 3.67br-s4H,3.77s2H,5.08d(5Hz) 1H,5.62q(9;5Hz)1H,6.8–7.5m2H, 7.75br-s2H,8.63s1H,9.07d(9Hz) 1H. | — |
| 30 | thiophene-CH₂CO— | =NN=C(NH₂)-N(morpholine) 1/2HI | 3.63br-s8H,3.78s2H,3.95ABq(58; 18Hz)2H,5.15d(5Hz)1H,5.67dd(8; 5Hz)1H,6.8–7.5m3H,7.98brs2H, 8.58s1H,9.10d(8Hz)1H. | −387.6° 0.375DMSO 23° C |
| 31 | thiophene-CH₂CO— | =NN=C(NH₂CH₃)-N(morpholine) 1/2HI H₂O | 1.18t(7Hz)3H,5.12d(5Hz)1H,5.65 m1H,6.77–7.48m3H,8.60s1H,9.08d (8Hz)1H. | −387.6° 0.375DMSO 23° C |
| 32 | thiophene-CH₂CO— | =NN=C-NH₂ 1/2HBr 1/2H₂O (morpholine-CH₃) | 1.12d(6Hz)3H,3.78s,3.2–4.5m 9H,5.12d(5Hz)1H,5.65q(8;5Hz) 1H,6.8–7.5m3H,7.90brs1-2H,8.58 s1H,9.08d(8Hz)1H. | — |
| 33 | thiophene-CH₂CO— | =NN=C(NH₂)-N(CH₃-morpholine) | 1.23d(4Hz)3H,5-13d(5Hz)1H,5.68 br1H,6.8–7.5m3H,7.97brs2H,8.57 s1H,9.12d(10Hz)1H. | −294.4° 0.481DMSO 24.5° C |
| 34 | thiophene-CH₂CO— | =NN=C(NH₂)-N(CH₃,CH₃-morpholine) | 0.9–1.4br6H,5.15d(4Hz)1H,6.8– 7.5m3H,7.95br2H,8.55brs1H,9.12 d(8Hz)1H. | −257.7° 0.456DMSO 24.5° C |
| 35 | thiophene-CH₂CO— | =NN=C(NH₂)-N(CH₃,CH₃-morpholine) H₂O | 1.10d(5.5Hz)6H,5.08d(5Hz)1H, 5.60dd(8;5Hz)1H,6.85–7.45m3H, 8.62s1H,9.03d(8Hz)1H. | −296° 0.075CH₃OH 24.5° C |
| 36 | thiophene-CH₂CO— | =NN=C(NH₂)-N(oxazine) | 1.77br4H,3.3–4.3br8H,5.17d(4 Hz)1H,5.70q(8;4Hz)1H,6.8–7.5m 3H,7.7–8.2br2H,8.55s1H,9.10d1H. | −197.3° 0.525DMSO 24.5° C |
| 37 | thiophene-CH₂CO— | =NN=C(NH₂)-N(morpholine-fused) | 1.4–2.0br2H,3.2–4.3br8H,4.8– 5.4br3H,5.5–5.8br1H,6.7–7.5m 3H,7.8–8.2br2H,8.6br-s1H,8.9– 9.2br1H. | −227.2° 0.529DMSO 23.5° C |
| 38 | thiophene-CH₂CO— | =NN=C(NH₂)-N(thiazolidine) | 5.15d(4Hz)1H,5.70dd(8;4Hz)1H, 6.8–7.5m3H,7.88s1H,8.63s1H, 9.18d(8Hz)1H. | −277.7° 0.439DMSO 24.5° C |

TABLE II-continued
| Compound No. | Acyl | =Z | NMR: δd₆-DMSO (60 MHz) (Values in ( ) show coupling consts.) | [α]$_D^{t\,°C}$ (c) |
|---|---|---|---|---|
| 39 | 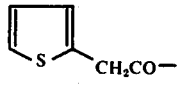 | 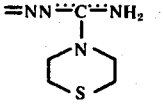 | 5.13d(5Hz)1H,5.67dd(8;5Hz)1H, 6.7–7.5m3H,7.93brs1H,8.60s1H, 9.10d(8Hz)1H. | −270.7° 0.430DMSO 24.0° C |
| 40 | 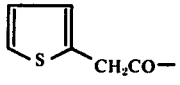 | 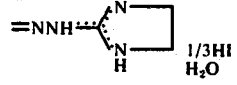 1/3HI H₂O | 5.15d(5Hz)1H,5.60dd(5;8Hz)1H, 6.8–7.5m3H,9.07s1H,9.15d(8Hz) 1H. | +119.6° 0.520DMSO 24.0° C |
| 41 | 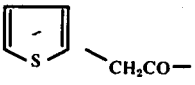 | 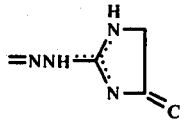 | — | — |
| 42 | H— | 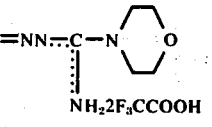 NH₂ 2F₃CCOOH | — | — |
| 43 | C₆H₅OCH₂CO— | 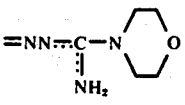 NH₂ | — | — |
| 44 | 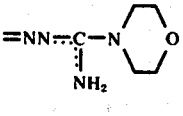 | | | |
| 45 | C₆H₅CHCO— NH₂ CF₃COOH | 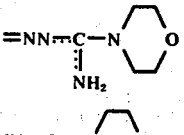 NH₂ | 3.63br6H,5.08br1H,5.82br1H, 7.47s5H,8.13br2H,8.47br1H,9.58 d(9Hz)1H. | — |
| 46 | C₆H₅CHCO— NHCOO tert-C₄H₉ | 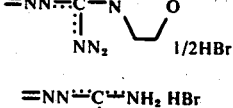 NH₂ | — | — |
| 47 | C₆H₅CH₂CO— | 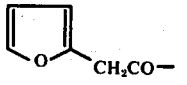 NN₂   1/2HBr | — | — |
| 48 | 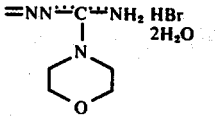 | 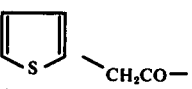 | — | −558.6° 0.531DMSO 22.5° C |
| 49 | 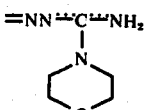 | 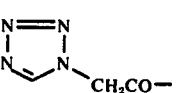 | — | −389.6° 0.316DMSO 23° C |
| 50 | 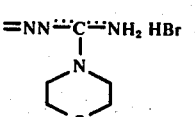 | =NN═C═NH₂ HBr <br>morpholine | — | — |
| 51 | (CH₃)₃C—OCO— | 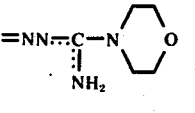 NH₂ | — | — |

TABLE II-continued

| Compound No. | Acyl | =Z | NMR: $\delta d_6$-DMSO (60 MHz) (Values in ( ) show coupling consts.) | $[\alpha]_D^{t°C}$ (c) |
|---|---|---|---|---|
| 52 | Cl₃CCH₂OCO— | =NN=C(NH₂)—N(morpholine) | — | — |
| 53 | 2-NO₂-C₆H₄-S— (7α—CH₃O derivative) | =NN=C(NH₂)—N(morpholine) | — | — |
| 54 | 2-thienyl-CH₂CO— (R = CH₃) | =NN=C(NH₂)—N(morpholine) | — | — |
| 55 | 2-thienyl-CH₂CO— | =NN=C(NH₂)—NHNO₂ | — | — |
| 56 | 2-thienyl-CH₂CO— | =NN=C(NH₂)—N(OH)CH₃ | — | −194.3° 0.492DMSO 23.5° C |
| 57 | 2-thienyl-CH₂CO— | =NN=C(NH₂)—N(OCH₃)CH₃ | — | — |
| 58 | 2-thienyl-CH₂CO— | =NN=C—NNH₂ / N-NH / =S | 3.58s2H,5.20d(5Hz)1H,5.57dd(8; 5Hz)1H,6.8–7.5m3H,8.50s1H,9.17 d(8Hz)1H,11.03s1H. | −205° 0.308DMSO 25° C |

EXAMPLE I-3.

In a procedure similar to that in Example I-2, the following compounds are prepared:

1. 3-[4,4-(3-azapentamethylene)guanylhydrazono]-methyl-7-(2-thienylacetamido)-3-cephem-4-carboxylic acid,
2. 3-[4,4-(3-acetylazapetamethylene)guanylhydrazono]methyl-7-(2-thienylacetamido)-3-cephem-4-carboxylic acid,
3. 3-[4,4-(2-hydroxytetramethylene)guanylhydrazono]methyl-7-(2-thienylacetamido)-3-cephem-4-carboxylic acid,
4. 3-[4,4-(1-methylpentamethylene)guanylhydrazono]methyl-7-(2-thienylacetamido)-3-cephem-4-carboxylic acid,
5. 3-[4,4-(4-methyl-3-oxapentamethylene)guanylhydrazono]methyl-7-phenylacetamido-3-cephem-4-carboxylic acid,
6. 3-[4,4-(3-thiapentamethylene)guanylhydrazono]-methyl-7-phenylacetamido-3-cephem-4-carboxylic acid,
7. 3-(4-phenylguanylhydrazono)methyl-7-(2-thienylacetamido)-3-cephem-4-carboxylic acid,
8. 3-[3-methyl-4,4-(3oxapentamethylene)guanylhydrazono]methyl-7-(2-thienylacetamido)-3-cephem-4-carboxylic acid,
9. 3-[4,4-dimethyl-3,3-(3,3(3-oxapentamethylene)-guanylhydrazono]methyl-7-phenylacetamido-3-cephem-4-carboxylic acid,
10. 3-(4,4-diallylguanylhydrazono)methyl-7-(2-thienylacetamido)-3-cephem-4-carboxylic acid,
11. 3-[4,4-(3-oxapentamethylene)guanylhydrazono]-methyl-7-(α-phenyl-α-carboxyacetamido)-3-cephem-4-carboxylic acid,
12. 3-(4-nitroguanylhydrazono)methyl-7-(1-tetrazolylacetamido)-3-cephem-4-carboxylic acid,
13. 3-[4,4-(3-oxapentamethylene)guanylhydrazono]-methyl-7-(3-isoxazolylacetamido)-3-cephem-4-carboxylic acid,
14. 3-(4,4-dimethylguanylhydrazono)methyl-7-mandelamido-3-cephem-4-carboxylic acid, and
15. 3-[4,4-(3-oxapentamethylene)guanylhydrazono]-methyl-7-(α-sulfo-α-phenylacetamido)-3-cephem-4-carboxylic acid.

EXAMPLE II-1.

To a solution of 7-amino-3-[4,4-(3-oxapentamethylene)guanylhydrazono]methyl-3-cephem-4-carboxylic acid (35 mg) and triethylamine (0.02 ml) in dimethyl sulfoxide (5 ml) is added N-carbethoxyphthalimide (23 mg), and the mixture is kept at room temperature for 18 hours. The reaction mixture is diluted with a mixture of water and ethyl acetate, and the organic layer is removed. The aqueous layer is acidified with hydrochloric acid to pH 1.5, and is extracted with ethyl acetate. The extract solution is washed with water, dried, and evaporated. The obtained residue is stirred in ethyl acetate to give 3-[4,4-(3-oxapentamethylene)guanylhydrazono]methyl-7-phthalimido-3- cephem-4-carboxylic acid. IR: $\nu_{max}^{Nujol}$ 1790, 1730 cm$^{-1}$.

EXAMPLE II-2.

In a procedure conventional in the art, following reactions are carried out to give the desired products:
1. 7-amino-3-[4,4-(3-oxapentamethylene)guanylhydrazono]methyl-3-cephem-4-carboxylic acid (36 mg), triethylamine (0.03 ml), and 2-thienylacetyl chloride in methylene chloride give 3-[4,4-(3-oxapentamethylene)guanylhydrazono]methyl-7-(2-thienylacetamido)-3-cephem-4-carboxylic acid hemihydrate (40 mg), m.p. 214°–218° C (decomp.). Yield: 83%;
2. diphenylmethyl 7-amino-3-[4,4-(3-oxapentamethylene)guanylhydrazono]methyl-3-cephem-4-carboxylate 1-oxide (78 mg), 2-thienylacetic acid (23 mg), and N,N'-dicyclohexylcarbodiimide (33 mg), in tetrahydrofuran give diphenylmethyl 3-[4,4-(3-oxapentamethylene)guanylhydrazono]methyl-7-(2-thienylacetamido)-3-cephem-4-carboxylate 1-oxide monohydrate (80 mg), m.p. 185°–188° C (decomp.), Yield: 81%;
3. 7-amino-3-[4,4-(3-oxapentamethylene)guanylhydrazono]methyl-3-cephem-4-carboxylic acid (36 mg), triethylamine (0.015 ml), and 2,4-dinitrophenyl phenoxyacetate in methylene chloride give 3-[4,4-(3-oxapentamethylene)guanylhydrazono]methyl-7-phenoxyacetamido-3-cephem-4-carboxylic acid (31 mg), m.p. 175°–185° C (decomp.), Yield: 63%;
4. 7-amino-3-[4,4-(3-oxapentamethylene)guanylhydrazono]methyl-3-cephem-4-carboxylic acid (70 mg), triethylamine (0.05 ml), and 2-thienylacetic isobutoxyformic mixed anhydride in methylene chloride give 3-[4,4-(3-oxapentamethylene)guanylhydrazone]methyl-7-(2-thienylacetamido)-3-cephem-4-carboxylic acid hemihydrate (63 mg), m.p. 215°–217° C (decomp.), Yield: 65%, and
5. p-nitrobenzyl 7-amino-3-[4,4-(3-oxapentamethylene)guanylhydrazono]methyl-3-cephem-4-carboxylate (24 mg), pyridine, and acetyl chloride (11 μl) give p-nitrobenzyl 7-acetamido-3-[4,4-(3-oxapentamethylene)guanylhydrazono]methyl-3-cephem-4-carboxylate (14 mg), m.p. 226°–231° C (decomp.), Yield: 53.8%;

EXAMPLE II-3.

In a procedure similar to those in Example II-2, the objective compounds of Examples from I-1 to I-3 are prepared starting from the corresponding 7-amino-3-guanylhydrazonomethyl-3-cephem-4-carboxylic acid derivatives.

EXAMPLE III-1.

A mixture of p-nitrobenzyl 3-[4,4-(3-oxapentamethylene)-guanylhydrazono]methyl-7-tertiary butoxycarbonylamino-3-cephem-4-carboxylate (75 mg), ice cooled trifluoroacetic acid (0.7 ml), and anisole (0.35 ml) is kept at room temperature for 35 minutes. The reaction is evaporated, the obtained residue is disolved in a mixture of water (1.5 ml) and ethyl acetate (4 ml), and made alkaline with aqueous sodium hydrogen carbonate. The solution is extracted with ethyl acetate, and the extract is washed with water, dried, and evaporated. Recrystallization of the obtained residue from methanol gives p-nitrobenzyl 7-amino-3-[4,4-(3-oxapentamethylene)guanylhydrazpono]methyl-3-cephem-4-carboxylate (26 mg). m.p. 115°–125° C/142°–152° C (decomp.). Yield: 41.7%. IR: $\nu_{max}^{CHCl_3}$ 3405, 3390, 1780, 1731, 1599, 1501, 1350 cm$^{-1}$ NMR: $\delta^{CDCl_3+CD_3OD}$ 3.4–3.9br6H, 4.88d(4Hz)1H 5.15d(4Hz)1H, 5.47s 2H, 7.68d(8Hz)2H 8.28d(8Hz)2H, 8.55s1H.

EXAMPLE III-2.

b 1. Hydrolysis of 3-[4,4-(3-oxapentamethylene)-guanylhydrazono]methyl-7-(tertiary butoxycarbonyl)amino-3-cephem-4-carbpxu;oc acid (205 mg) with trifluoroacetic acid (2 ml) and anisole (1 ml) at room temperature for 30 minutes gives 7-amino-3-[4,4-(3-oxapentamethylene)guanylhydrazono]methyl-3-cephem-4-carboxylic acid di-trifluoroacetate (240 mg) m.p. 230°–250° C (decomp.). Yield: 91.4%.
2. Hydrolysis of sodium 3-[4,4-(3-oxapentamethylene)guanylhydrazono]methyl-7-(o-nitrophenylsulfenyl)amino-3-cephem-4-carboxylate (45 mg) with hydrochloric acid and potassium iodide in 75% dioxane (1 ml) at pH about 3 and at room temperature gives 7-amino-3-[4,4-(3-oxapentamethylene)guanylhydrazono]methyl-3-cephem-4-carboxylic acid.
3. Reductive fission of diophenylmethyl 3-[4,4-(3-oxapentamethylene)guanylhydrazono]methyl-7-(2,2,2-trichloroethoxycarbonyl)amino-3-cephem-4-carboxylate (30 mg) with zinc dust (100 mg) in 90% acetic acid (1 ml) gives diphenylmethyl 7-amino-3-[4,4-(3-oxapentamethylene)guanylhydrazono]methyl-3-cephem-4-carboxylate.

EXAMPLE IV-1.

To stirred suspension of 3-[4,4-(3-oxapentamethylene)guanylhydrazono]methyl-7-(2-thienylacetamido]-3-cephem-4-carboxylic acid hemihydrobromide dihydrate (333 mg) in water (7.5 ml) is added 1N-aqueous sodium hydroxide (0.7 ml) at 0° C to pH 10.5. After removing minor quantity of solid material, the solution is lyophillized to give sodium 3-[4,4-(3-oxapentamethylene)guanylhydrazono]methyl-7-(2-thienylacetamido)-3-cephem-4-carboxylate (340 mg). m.p. 190°–215° C (decomp.). Yield: 98%.

EXAMPLE IV-2.

A solution of the objective compounds (1 mole equivalent) of Examples from I-2 to 3 in 0.1 M aqueous sodium hydrogen carbonate (1 mole equivalent) is lyophillized to give the corresponding sodium salts. The sodium salts are soluble in water, and used for estimation of antibacterial activity.

EXAMPLE V-1.

A solution of diphenylmethyl 3-[4,4-(3-oxapentamethylene)guanylhydrazono]methyl-7-(2-thienylacetamido)-3-cephem-4-carboxylate (129 mg) in a mixture of anisole (0.2 ml) and trifluoroacetic acid (0.2 ml) is kept at room temperature for 2 hours. The reaction mixture is evaporated, and resulted residue is let standing in ether. The formed crystals are collected by filtration, and to give 3-[4,4-(3-oxapentamethylene)guanylhydrazono]methyl-7-(2-thienylacetamido)-3-cephem-4-carboxylic acid hemihydrarte (86 mg). m.p. 215°–217° C (decomp.). Yield: 96%.

EXAMPLE V-2.

To a solution of sodium 3-[4,4-(3-oxapentamethylene)guanylhydrazono]methyl-7-(2-thienylacetamido)-3-cephem-4-carboxylate (50 mg) in water (2 ml) is added 0.1N hydrochloric acid (0.1 ml), and the mixture is kept at room temperature overnight. The formed crystals are collected by filtration, washed with water and anhydrous ether, and dried to give 3-[4,4-(3-oxapentamethylene)guanylhydrazono]methyl-7-(2-thienylacetamido)-3-cephem-4-carboxylic acid hemihydrate (47 mg). m.p. 215°–217° C (decomp.). Yield: 98%.

EXAMPLE VI-1.

To a solution of diphenylmethyl 3-[4,4-(3-oxapentamethylene)guanylhydrazono]methyl-7-(2-thienylacetamido)-3-cephem-4-carboxylate (56 mg) in dioxane (5 ml) are added phosphate buffer (pH 6; 1 ml) and 0.25 M aqueous sodium periodate (0.32 ml), and the mixture is stirred for 4 hours. The reaction mixture is evaporated, and the obtained residue is dissolved in ethyl acetate, washed with water, dried, and evaporated. Stirring the residue in ether gives diphenylmethyl 3-[4,4-(3-oxapentamethylene)guanylhydrazono]methyl-7-(2-thienylacetamido)-3-cephem-4-carboxylate 1-oxide (30 mg). m.p. 185°–188° C (decomp.). Yield: 52%.

EXAMPLE VII-1.

To a solution of methyl 3-[4,4-(3-oxapentamethylene)guanylhydrazono]methyl-7-phthalimido-3-cephem-4-carboxylate 1-oxide (64 mg) in N,N-dimethylformamide (2 ml) containing stannous chloride dihydrate (45 mg) is added acetyl chloride (0.1 ml), and the mixture is stirred for 2 hours under ice cooling. The reaction mixture is diluted with ice water, and extracted with ethyl acetate. The extract solution is washed with aqueous sodium hydrogen carbonate and water, dried and evaporated. Stirring of the residue in a mixture of ethyl acetate and ether separates crystals which are collected by filtration, and dried to give methyl 3-[4,4-(3-oxapentamethylene)guanylhydrazono]methyl-7-phthalimido-3-cephem-4-carboxylate (50 mg). m.p. 247°–252° C (decomp.). Yield: 80%.

EXAMPLE VIII-1.

To a solution of 3-[4,4-(3-oxapentamethylene)guanylhydrazono]methyl-7-(α-phenylglycyl)amino-3-cephem-4-carboxylic acid (47 mg) and triethylamine (0.02 ml) in water (0.2 ml) is added a solution of O-tertiary butyl S-(4,6-dimethyl-2-pyrimidyl) thiocarbonate (30 mg) in dioxane (0.2 ml), and the mixture is stirred at room temperature for 16 hours. The reaction mixture is concentrated to remove dioxane, and the resulting solution is diluted with water, and is washed with ethyl acetate. The aqueous layer is acidified with hydrochloric acid to pH 1.5, and extracted with ethyl acetate. The extract solution is washed with saturated saline, dried, and concentrated. Stirring of the residue in ether gives 3-[4,4-(3-oxapentamethylene)guanylhydrazono]methyl-7-(α-phenyl-N-tertiary butoxycarbonylglycyl)amino-3-cephem-4-carboxylic acid (43 mg). m.p. 227°–235° C (decomp.). Yield: 75%.

EXAMPLE VIII-2.

To a stirred suspension of 3-[4,4-(3-oxapentamethylene)guanylhydrazono]methyl-7-(2-thienylacetamido)-3-cephem-4-carboxylic acid hemihydrobromide dihydrate (111 mg) in water (2.5 ml) is added at 0° C, 0.1N aqueous sodium hydroxide (1 ml) to pH about 7, and the solution is kept at room temperature overnight. The separated white precipitate is washed with water, and dried to give 3-[4,4-(3-oxapentamethylene)guanylhydrazono]methyl-7-(2-thienylacetamido)-3-cephem-4-carboxylic acid hemihydrate (100 mg). m.p. 215°–217° C (decomp.). Yield: 97%.

EXAMPLE VIII-3.

To a solution of 3-[4,4-(3-oxapentamethylene)guanylhydrazono]methyl-7-(α-phenyl-N-tertiary butoxycarbonylglycyl)amino-3-cephem-4-carboxylic acid (56 mg) in methylene chloride (0.6 ml) are added anisole (0.1 ml) and trifluoroacetic acid (0.1 ml), and the mixture is kept at room temperature for 1 hour. After 1 hour and 2 hours, 0.2 ml each of trifluoroacetic acid is added to the mixture, and 15 minutes after the final addition, the reaction mixture is evaporated. Addition of ether (1 ml) to the obtained residue gives crystals which are collected by filtration, washed with ether, and dried to give 3-[4,4-(3-oxapentamethylene)guanylhydrazono]methyl-7-(α-phenylglycyl)amino-3-cephem-4-carboxylic acid trifluoroacetate (56 mg.) m.p. 225°–235° C (decomp.). Yield: 98%.

EXAMPLE VIII-4.

A solution of 3-[4,4-(3-oxapentamethylene)guanylhydrazono]methyl-7-(α-phenylglycyl)amino-3-cephem-4-carboxylic acid trifluoroacetate (50 mg) in water (0.5 ml) is poured into 25% solution of Amberlite LA-1 in methyl isobutyl ketone (0.5 ml), and the mixture is stirred at room temperature for 1 hour. The separated crystals are collected by filtration, washed with water and methyl isobutyl ketone, and dried to give 3-[4,4-(3-oxapentamethylene)guanylhydrazono]methyl-7-(α-phenylglycyl)amino-3-cephem-4-carboxylic acid (45 mg). IR: $\nu_{max}^{Nujol}$ 3250, 1773, 1675, 1640 cm$^{-1}$.

Preparation I.

Sterilized microcrystals of sodium 7-(2-thienylacetamido)-3-[4,4-(3-oxapentamethylene)-guanylhydrazono]methyl-3-cephem-4-carboxylate (0.5 g) placed in a vial filled with nitrogen are dissolved in water (4 ml) and given to a patient infected by a sensitive strain of Proteus mirabilis twice to four times a day.

PREPARATION II

Sterilized lyophillizate of sodium 7-(2-thienylacetamido)-3-[4,4-(3-oxapentamethylene)-guanylhydrazono]methyl-3-cephem-4-carboxylate (0.2 g) placed in a vial filled with nitrogen are dissolved in water (2 ml) and given to a patient infected by a sensitive strain of Streptococcus faecalis twice to four times a day.

What we claim is:

1. A member of the group consisting of a compound of the formula

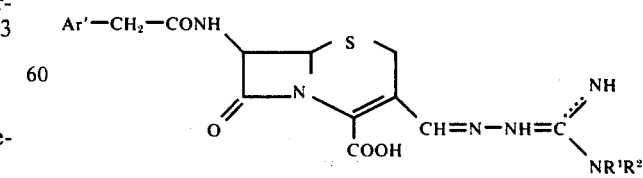

wherein
Ar' represents a member selected from the group of furyl, thienyl, pyrryl, oxazolyl, isoxazoyl, oxadiazolyl, oxatriazolyl and said groups substituted by a hydroxy, halogen or methyl group, and
—NR¹R² is a ring system group selected from the following groups (1) pyrrolidin-1-yl, (2) piperidin-1-yl, (3) 1-azacycloheptan-1yel, (4) pyrrolin-1-yl, (5) tetrahydropyridin-1-yl, (6) morpholin-4-yl, (7) tetrahydro-1,2-oxazin-2-yl, (8) tetrahydro-1,3-oxazin-3-yl, (9) tetrahydroisoxazol-2-yl, (10) tetrahydrooxazol-3-yl, (11) tetrahydroisothiazol-2-yl, (12) tetrahydrothiazol-3-yl, (13) tetrahydro-1,3-thiazin-3-yl, and (14) tetrahydro-1,4-thiazin-4-yl, said groups being unsubstituted or substituted by a member selected from the group consisting of alkyl of 1 to 6 carbon atoms, oxo, hydroxy, halogen, carbalkoxy, and carbamoyl and a pharmaceutically acceptable salt thereof.

2. A member of the group consisting of a compound of the formula

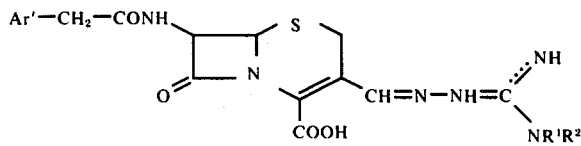

wherein
Ar' represents a member selected from the group of furyl, thienyl, pyrryl, oxazolyl, isoxazoyl, oxadiazolyl, oxatriazolyl and said groups substituted by a hydroxy, halogen or methyl group,
—NR¹R² is a ring system group selected from the following groups: (1) pyrrolidin-1-yl, (2) piperidin-1-yl, (3) 1-azacycloheIptan-1-yl, (4) pyrrolin-1-yl, (5) tetrahydropyridin-1-yl, (6) morpholin-4-yl, (7) tetrahydro-1,2-oxazin-2-yl, (8) tetrahydro-1,3-oxazin-3-yl, (9) tetrahydroisoxazol-2-yl, (10) tetrahydrooxazol-3-yl, (11) tetrahydroisothiazol-2-yl, (12) tetrahydrothiazol-3-yl, (13) tetrahydro-1,3-thiazin-3-yl, and (14) tetrahydro-1,4-thiazin-4-yl, and a pharmaceutically acceptable salt thereof.

3. A compound according to claim 1 wherein Ar' is thienyl.

4. A compound according to claim 1 wherein —NR¹R² is a tetrahydro-1,4-oxazin-4-yl ring system group.

5. A compound according to claim 1 selected from the group consisting of:
7-(2-thienylacetamido)-3-[4,4-(3-oxapentamethylene)guanylhydrazono]methyl-3-cephem-4-carboxylic acid,
7-(2-thienylacetamido)-3-[4,4-(1-methyl-3-oxapentamethylene)guanylhydrazono]methyl-3-cephem-4-carboxylic acid,
7-(2-thienylacetamido)-3-[4,4-(2-methyl-3-oxapentamethylene)guanylhydrazono]methyl-3-cephem-4-carboxylic acid,
7-(2-thienylacetamido)-3-[4,4-(1,4-dimethyl-3-oxapentamethylene)guanylhydrazono]methyl-3-cephem-4-carboxylic acid,
7-(2-thienylacetamido)-3-[4,4-(2,4-dimethyl-3-oxapentamethylene)guanylhydrazono]methyl-3-cephem-4-carboxylic acid,
7-(2-thienylacetamido)-3-[4,4-(2-ethyl-3-oxapentamethylene)guanylhydrazono]methyl-3-cephem-4-carboxylic acid,
7-(2-furylacetamido)-3-[4,4-(3-oxapentamethylene)guanylhydrazono]methyl-3-cephem-4-carboxylic acid,
7-(3-thienylacetamido)-3-[4,4-(3-oxapentamethylene)guanylhydrazono]methyl-3-cephem-4-carboxylic acid,
7-(3-isoxazolylacetamido)-3-[4,4-(3-oxapentamethylene)guanylhydrazono]methyl-3-cephem-4-carboxylic acid.

6. A compound according to claim 1 wherein —NR¹R² is a pyrrolidin-1-yl, piperidin-1-yl, or 1-azacycloheptan-1-yl ring system group.

7. A compound according to claim 1 selected from the group consisting of:
7-(2-thienylacetamido)-3-(4,4-tetramethyleneguanylhydrazono)methyl-3-cephem-4-carboxylic acid,
7-(2-thienylacetamido)-3-(4,4-pentamethyleneguanhylhydrazono)methyl-3-cephem-4-carboxylic acid,
7-(2-thienylacetamido)-3-(4,4-hexamethyleneguanylhydrazono)methyl-3-cephem-4-carboxylic acid.

8. A compound according to claim 1 wherein —NR¹R² is a pyrrolin-1-yl or tetrahydropyridin-1-yl ring system group.

9. A compound according to claim 1 selected from the group consisting of:
7-(2-thienylacetamido)-3-[4,4-(but-2-en-1,4-diyl)-guanylhydrazono]methyl-3-cephem-4-carboxylic acid,
7-(2-thienylacetamido)-3-[4,4-(pent-2-en-1,5-diyl)-guanylhydrazono]methyl-3-cephem-4-carboxylic acid.

10. A compound according to claim 1 wherein —NR¹R² is a tetrahydro-1,2-oxazin-2-yl, tetrahydro-1,3-oxazin-3-yl, tetrahydro-1,4-thiazin-4yl, tetrahydrothiazol-3-yl, tetrahydroisoxazol-2-yl, tetrahydrooxazol-3-yl, or tetrahydroisothiazol-2-yl ring system group.

11. A compound according to claim 1 selected from the group consisting of:
7-(2-thienylacetamido)-3-[4,4-(1-oxapentamethylene)guanylhydrazono]methyl-3-cephem-4-carboxylic acid,
7-(2-thienylacetamido)-3-[4,4-(2-oxapentamethylene)guanylhydrazono]methyl-3-cephem-4-carboxylic acid,
7-(2-thienylacetamido)-3-[4,4-(2-thiatetramethylene)guanylhydrazono]methyl-3-cephem-3-carb oxylic acid,
7-(2-thienylacetamido)-3-[4,4-(3-thiapentamethylene)guanylhydrazono]methyl-3-cephem-4-carboxylic acid,
7-(2-thienylacetamido)-3-[4,4-(1-oxatetramethylene)guanylhydrazono]methyl-3-cephem-4-carboxylic acid,
7-(2-thienylacetamido)-3-[4,4- (2-oxatetramethylene)guanylhydrazono]methyl-3-cephem-4-carboxylic acid.

12. A compound according to claim 1 said compound being 7-(3-thienylacetamido)-3-[4,4-(3-oxapentamethylene)guanylhydrazono]methyl-3-cephem-4-carboxylic acid.

* * * * *